US009403788B2

(12) United States Patent
Lee et al.

(10) Patent No.: US 9,403,788 B2
(45) Date of Patent: Aug. 2, 2016

(54) PROCESS FOR THE PRODUCTION OF ACID ANHYDRIDES FROM EPOXIDES

(71) Applicant: Novomer, Inc., Ithaca, NY (US)

(72) Inventors: Han Lee, Ithaca, NY (US); Michael A. Slowik, Ithaca, NY (US)

(73) Assignee: NOVOMER, INC., Ithaca, NY (US)

( * ) Notice: Subject to any disclaimer, the term of this patent is extended or adjusted under 35 U.S.C. 154(b) by 0 days.

(21) Appl. No.: 14/378,290

(22) PCT Filed: Feb. 12, 2013

(86) PCT No.: PCT/US2013/025683
§ 371 (c)(1),
(2) Date: Aug. 12, 2014

(87) PCT Pub. No.: WO2013/122905
PCT Pub. Date: Aug. 22, 2013

(65) Prior Publication Data
US 2015/0005513 A1    Jan. 1, 2015

Related U.S. Application Data

(60) Provisional application No. 61/597,863, filed on Feb. 13, 2012.

(51) Int. Cl.
| | | |
|---|---|---|
| C07D 307/60 | (2006.01) |
| C07D 303/12 | (2006.01) |
| B01J 31/22 | (2006.01) |
| C07D 305/12 | (2006.01) |

(52) U.S. Cl.
CPC ........... *C07D 307/60* (2013.01); *B01J 31/2295* (2013.01); *C07D 303/12* (2013.01); *C07D 305/12* (2013.01); *B01J 2231/48* (2013.01); *B01J 2531/31* (2013.01); *B01J 2531/845* (2013.01)

(58) Field of Classification Search
CPC .................................................... C07D 307/60
USPC ................................................. 549/231, 233
See application file for complete search history.

(56) References Cited

U.S. PATENT DOCUMENTS

| | | | |
|---|---|---|---|
| 2,245,404 A * | 6/1941 | Kise et al. ..................... 549/233 |
| 2,469,704 A | 5/1949 | Stone |
| 3,326,938 A | 6/1967 | Wagner |
| 3,751,435 A | 8/1973 | Van der Ven et al. |
| 4,590,293 A | 5/1986 | Pascoe |
| 4,873,378 A | 10/1989 | Murphy et al. |
| 6,392,078 B1 | 5/2002 | Ryu et al. |
| 6,852,865 B2 | 2/2005 | Coates et al. |
| 6,916,951 B2 | 7/2005 | Tustin et al. |
| 7,714,165 B2 * | 5/2010 | Broell et al. ................ 562/892 |
| 8,084,640 B2 * | 12/2011 | Broell et al. ................ 562/888 |
| 9,156,803 B2 | 10/2015 | Allen et al. |
| 2003/0098274 A1 | 5/2003 | Lee et al. |
| 2003/0162961 A1 | 8/2003 | Coates et al. |
| 2005/0014977 A1 | 1/2005 | Drent et al. |
| 2005/0240032 A1 | 10/2005 | Luinstra et al. |
| 2007/0217965 A1 | 9/2007 | Johnson et al. |
| 2007/0293695 A1 | 12/2007 | Zoeller et al. |
| 2009/0124787 A1 | 5/2009 | Preishuber-Pflugl et al. |
| 2009/0253934 A1 | 10/2009 | Ho et al. |
| 2012/0123137 A1 | 5/2012 | Allen et al. |
| 2013/0165670 A1 | 6/2013 | Allen et al. |

FOREIGN PATENT DOCUMENTS

| | | |
|---|---|---|
| EP | 0352850 A1 | 1/1990 |
| EP | 0441447 A1 | 8/1991 |
| EP | 2325214 A1 | 5/2011 |
| WO | WO-2010/118128 A1 | 10/2010 |
| WO | WO-2012/030619 A1 | 3/2012 |
| WO | WO-2013/063191 A1 | 5/2013 |
| WO | WO-2013/122905 A1 | 8/2013 |
| WO | WO-2013/126375 A1 | 8/2013 |
| WO | WO-2014/008232 A2 | 1/2014 |

OTHER PUBLICATIONS

Rowley et al., Catalytic Double Carbonylation of Epoxides to Succinic Anhydrides: Catalyst Discovery, Reaction Scope, and Mechanism, Journal of American Chemical Society, 129:4948-4960 (2007).
International Search Report for PCT/US2013/025683, 2 pages (Apr. 23, 2013).
Written Opinion for PCT/US2013/025683, 10 pages (Apr. 23, 2013).
International Search Report for PCT/US13/26810, 2 pages (Apr. 3, 2013).
International Search Report for PCT/US2013/049026, 2 pages (Dec. 17, 2013).
International Search Report of PCT/US10/30230, 3 pages (Jun. 10, 2010).
International Search Report of PCT/US12/61791, 3 pages (Feb. 8, 2013).
International Search Report of PCT/US2011/049125, 3 pages (received Jan. 11, 2012).
Slowik, et al., Catalytic conversion of waste carbon monoxide to valuable chemicals & materials, Technical Proceedings of the 2010 Clean Technology Conference and Trade Show, 283-286 (2010).
Written Opinion for PCT/US13/26810, 9 pages (Apr. 3, 2013).
Written Opinion for PCT/US2013/049026, 6 pages (Dec. 17, 2013).
Written Opinion of PCT/US10/30230, 13 pages (Jun. 10, 2010).
Written Opinion of PCT/US12/61791, 6 pages (Feb. 8, 2013).
Written Opinion of PCT/US2011/049125, 10 pages (received Jan. 11, 2012).

* cited by examiner

*Primary Examiner* — Golam M M Shameem
(74) *Attorney, Agent, or Firm* — Morrison & Foerster LLP

(57) ABSTRACT

A method of making acid anhydrides from epoxide and carbon monoxide feedstocks is presented. In various aspects, the method includes steps of reacting the contents of a feed stream comprising an epoxide, a solvent, a carbonylation catalyst and carbon monoxide to produce a first carbonylation product stream comprising a beta-lactone, then reacting the contents of the first carbonylation product stream with additional carbon monoxide to produce a second carbonylation product stream comprising an acid anhydride, and separating at least a portion of the acid anhydride from the second carbonylation product stream to produce: i) an acid anhydride product stream comprising the separated portion of acid anhydride; and ii) a recycling stream comprising the carbonylation catalyst, and finally adding the recycling stream to the feed stream.

39 Claims, 6 Drawing Sheets

PROCESS FOR THE PRODUCTION OF ACID ANHYDRIDES FROM EPOXIDES

CROSS REFERENCE TO RELATED APPLICATIONS

The present application is the National Stage of International Application No. PCT/US2013/025683, filed Feb. 12, 2013, which claims priority to, and the benefit of, U.S. provisional application Ser. No. 61/597,863 filed Feb. 13, 2012, the entire content of both of which are hereby incorporated herein by reference.

BACKGROUND OF THE INVENTION

Acid anhydrides, in particular succinic anhydride, are valuable reactive intermediates commonly used in a variety of applications. For example, acid anhydrides are used in copolymers to produce biodegradable polyesters. Additionally, acid anhydrides are useful intermediates in organic synthesis because they are easily ring opened to form diacid monoesters, diacids or other derivatives. Succinic anhydride is particularly useful as a precursor to 4 carbon commodity chemicals such as tetrahydrofuran, gamma butyrolactone and 1,4-butanediol.

Previous production methods for acid anhydrides, including succinic anhydride, included dehydration of corresponding acids or hydrogenation of maleic anhydride. Additional production methods include catalyzed carbonylation of alkynes, alkenoic acids and lactones. Many of the methods suffered from low yield, production of many byproducts or lacked generality. Novel methods using more cost effective starting materials are sought.

SUMMARY OF THE INVENTION

In various embodiments of the present invention, a method of making acid anhydrides from epoxide and carbon monoxide feedstocks is presented. In some embodiments, the chemical reactions to convert the epoxide and carbon monoxide to an acid anhydride are catalyzed.

In various aspects, the present invention includes steps of reacting the contents of a feed stream comprising an epoxide, a solvent, a carbonylation catalyst and carbon monoxide to produce a first carbonylation product stream comprising a beta-lactone, then reacting the contents of the first carbonylation product stream with additional carbon monoxide to produce a second carbonylation product stream comprising an acid anhydride, and separating at least a portion of the acid anhydride from the second carbonylation product stream to produce: i) an acid anhydride product stream comprising the separated portion of acid anhydride; and ii) a recycling stream comprising the carbonylation catalyst, and finally adding the recycling stream to the feed stream.

In some embodiments, the step of separating at least a portion of the acid anhydride comprises separating solid acid anhydride from the second carbonylation product stream. In some embodiments, separation of solid acid anhydride comprises a step of exposing the second carbonylation product stream to conditions under which at least a portion of acid anhydride dissolved therein is not soluble. In some embodiments, the step of exposing the second carbonylation stream to conditions under which at least a portion of anhydride is not soluble comprises lowering the temperature of the product stream. In some embodiments, the step of exposing the second carbonylation stream to conditions under which at least a portion of anhydride is not soluble comprises reducing the pressure. In some embodiments, the step of exposing the second carbonylation stream to conditions under which at least a portion of anhydride is not soluble comprises lowering the partial pressure of CO. In some embodiments, the step of exposing the second carbonylation product stream to conditions under which at least a portion of anhydride is not soluble comprises adding one or more additional components to the stream. In some embodiments, an additional component added to the second carbonylation product stream comprises a solvent that lowers the solubility of the acid anhydride.

In some embodiments, the step of exposing the second carbonylation product stream to conditions under which at least a portion of anhydride is not soluble comprises adding solid acid anhydride as a crystallization nucleator. In some embodiments, substantially all of the carbonylation catalyst remains in solution. In some embodiments, the solid acid anhydride is separated by filtration to provide a solid as the acid anhydride product stream and a filtrate as the recycling stream. In some embodiments, the solid acid anhydride is separated by settling to provide a sediment as the acid anhydride product stream and a supernatant as the recycling stream.

In some embodiments, the method further includes a step of treating the recycling stream to increase the solubility of the acid anhydride prior to adding the recycling stream to the feed stream.

In some embodiments, the step of treating the recycling stream to increase the solubility of the acid anhydride comprises heating.

In some embodiments, the step of treating the recycling stream to increase the solubility of the acid anhydride comprises increasing the pressure. In some embodiments, the step of treating the recycling stream to increase the solubility of the acid anhydride comprises adding one or more additional components to the recycling stream. In some embodiments, the component added to the recycling stream comprises the epoxide.

In some embodiments, the step of separating at least a portion of the acid anhydride comprises partitioning the reaction mixture between two immiscible solvents, the immiscible solvents comprising a first solvent and a second solvent, wherein at least a portion of the succinic anhydride is partitioned into the first solvent, and a substantial portion of the catalyst is partitioned into the second solvent.

In some embodiments, the method further includes a step of physically separating the mixture of two immiscible solvents into which the second carbonylation product stream has been partitioned to provide a first solvent stream containing the first solvent and a second solvent stream containing the second solvent.

In some embodiments, the first solvent stream is the acid anhydride product stream and the second solvent stream becomes the recycling stream. In some embodiments, the solvent composition of the second solvent stream is changed prior to adding the recycling stream to the feed stream. In some embodiments, one of the two immiscible solvents comprises a substantial portion of the solvent present in the feed stream. In some embodiments, the second solvent substantially comprises the solvent present in the feed stream. In some embodiments, the method further includes a step of treating the first solvent stream to isolate the acid anhydride.

In some embodiments, the method further includes a step of treating the second solvent stream to obtain a carbonylation catalyst concentrate. In some embodiments, the carbonylation catalyst concentrate comprises a catalyst solution. In some embodiments, the recycling stream comprises the carbonylation catalyst concentrate. In some embodiments, the carbonylation catalyst concentrate comprises a solid.

In some embodiments, the method further includes dissolving the solid carbonylation catalyst concentrate in a solvent to provide the recycling stream.

In some embodiments, one of the immiscible solvents comprises an ionic liquid. In some embodiments, one of the immiscible solvents comprises an aqueous solvent. In some embodiments, the step of separating at least a portion of the acid anhydride comprises separating acid anhydride in the vapor phase. In some embodiments, a solvent in the feed stream has a vapor pressure lower than succinic anhydride.

In some embodiments, the step of separating at least a portion of the acid anhydride comprises heating the second carbonylation product stream. In some embodiments, the step separating at least a portion of the acid anhydride comprises exposing the second carbonylation product stream to reduced pressure.

In some embodiments, the first carbonylation step is performed in a first reaction zone and the second carbonylation step is performed in a second reaction zone wherein each reaction zone comprises one or more reactors. In some embodiments, a reactor in the first reaction zone and a reactor in the second reaction zone are of different design. In some embodiments, at least one reactor in the first reaction zone is operated under steady state reactor conditions. In some embodiments, at least one reactor in the second reaction zone is operated under non steady state reaction conditions. In some embodiments, the steady state conditions are maintained such that the first carbonylation product stream comprises at least some unreacted epoxide.

In some embodiments, the first carbonylation product stream comprises sufficient epoxide to prevent anhydride formation in the first reactor. In some embodiments, the first carbonylation product stream comprises at least about 5% epoxide. In some embodiments, the first carbonylation product stream comprises at least about 3% epoxide. In some embodiments, the first carbonylation product stream comprises at least about 2% epoxide. In some embodiments, the first carbonylation product stream comprises at least about 1% epoxide. In some embodiments, the first carbonylation product stream comprises at least about 0.5% epoxide. In some embodiments, the first carbonylation product stream comprises at least about 0.25% epoxide. In some embodiments, the first carbonylation product stream comprises at least about 0.1% epoxide.

In some embodiments, the first carbonylation step is performed in one or more continuous stirred tank reactors.

In some embodiments, the second carbonylation step is performed in one or more plug flow reactors. In some embodiments, the first carbonylation step is performed in an adiabatic reactor. In some embodiments, the first carbonylation reactor is a tubular reactor. In some embodiments, the first carbonylation reactor is a shell and tube reactor.

In some embodiments, the reaction conditions in the first reaction zone and the reaction conditions in the second reaction zone are different. In some embodiments, the pressure in the second reaction zone is different from the pressure in the first reaction zone. In some embodiments, the temperature in the second reaction zone is different from the temperature in the first reaction zone.

In some embodiments, the first carbonylation reaction is performed at a pressure from about 50 psi to about 5000 psi. In some embodiments, the first carbonylation reaction is performed at a pressure from about 50 psi to about 2000 psi. In some embodiments, the first carbonylation reaction is performed at a pressure from about 200 psi to about 1000 psi. In some embodiments, the first carbonylation reaction is performed at a pressure from about 200 psi to about 600 psi.

In some embodiments, the first carbonylation reaction is performed at a temperature from about 0° C. to about 125° C. In some embodiments, the first carbonylation reaction is performed at a temperature from about 30° C. to about 100° C. In some embodiments, the first carbonylation reaction is performed at a temperature from about 40° C. to about 80° C.

In some embodiments, the second carbonylation reaction is performed in an adiabatic reactor. In some embodiments, second carbonylation reactor is a tubular reactor. In some embodiments, the second carbonylation reactor is a shell and tube reactor.

In some embodiments, the second carbonylation reaction is performed at a pressure from about 50 psi to about 5000 psi. In some embodiments, the second carbonylation reaction is performed at a pressure from about 50 psi to about 2000 psi. In some embodiments, the second carbonylation reaction is performed at a pressure from about 200 psi to about 1000 psi. In some embodiments, the second carbonylation reaction is performed at a pressure from about 200 psi to about 600 psi.

In some embodiments, the second carbonylation reaction is performed at a temperature from about 0° C. to about 125° C. In some embodiments, the second carbonylation reaction is performed at a temperature from about 30° C. to about 100° C. In some embodiments, the second carbonylation reaction is performed at a temperature from about 40° C. to about 80° C.

In some embodiments, the carbon monoxide in either carbonylation reaction is supplied as an industrial gas stream comprising carbon monoxide and one or more additional gases. In some embodiments, the industrial gas stream comprises syngas. In some embodiments, the carbon monoxide in the reacting step is supplied in substantially pure form.

In some embodiments, the present invention further includes a step of converting the acid anhydride to a dicarboxylic acid product.

In some embodiments, the recycling stream comprises acid anhydride. In some embodiments, the feed stream is saturated with acid anhydride. In some embodiments, the first carbonylation reaction stream is saturated with acid anhydride.

In some embodiments, the epoxide is selected from the group consisting of ethylene oxide, propylene oxide, epichlorohydrin, a glycidol ester, a glycidol ester, 1,2-butylene oxide, 2,4 butylene oxide, an oxide of $C_{5-30}$ alpha olefin, and a mixture of any two or more of these. In some embodiments, the epoxide is ethylene epoxide.

In some embodiments, the acid anhydride is selected from the group consisting of succinic anhydride, methylsuccinic anhydride, chloromethylsuccinic anhydride, ethylsuccinic anhydride, or $C_{5-30}$ acid anhydrides. In some embodiments, the acid anhydride is succinic anhydride.

In some embodiments, the dicarboxylic acid is selected from the group consisting of succinic acid, methylsuccinic acid, chloromethylsuccinic acid, ethylsuccinic acid or $C_{5-30}$ dicarboxylic acids. In some embodiments, the dicarboxylic acid is succinic acid.

In some embodiments, the solvent is selected from the group consisting of 1,4-dioxane; 1,3-dioxane; tetrahydrofuran; tetrahydropyran; dimethoxyethane; glyme; diethyl ether; t-butyl methyl ether; 2,5-dimethyl tetrahydrofuran; ethyl acetate; propyl acetate; butyl acetate; acetone; 2-butanone; cyclohexanone; toluene; acetonitrile; difluorobenzene and combinations thereof. In some embodiments, the solvent is a strong Lewis base. In some embodiments, the solvent lacks a dipole moment. In some embodiments, the solvent is 1,4 dioxane.

In some embodiments, the carbonylation catalyst comprises a metal carbonyl compound. In some embodiments, the metal carbonyl compound has the general formula: $[QM_y(CO)_w]^x$, where: Q is any ligand and need not be present; M is a metal atom; y is an integer from 1 to 6 inclusive; w is a number such as to provide the stable metal carbonyl; and x is an integer from −3 to +3 inclusive.

In some embodiments, M is selected from the group consisting of Ti, Cr, Mn, Fe, Ru, Co, Rh, Ni, Pd, Cu, Zn, Al, Ga and In. In some embodiments, M is Co. In some embodiments, M is Co, y is 1, and w is 4. In some embodiments, the carbonylation catalyst further comprises a Lewis acidic co-catalyst. In some embodiments, the metal carbonyl compound is anionic, and the Lewis acidic co-catalyst is cationic.

In some embodiments, the metal carbonyl complex comprises a carbonyl cobaltate and the Lewis acidic co-catalyst comprises a metal-centered cationic Lewis acid. In some embodiments, the metal-centered cationic Lewis acid is a metal complex of formula $[M'(L)_b]^{c+}$, where, M' is a metal; each L is a ligand; b is an integer from 1 to 6 inclusive; c is 1, 2, or 3; and where, if more than one L is present, each L may be the same or different.

In some embodiments, M' is selected from the group consisting of: a transition metal, a group 13 or 14 metal, and a lanthanide. In some embodiments, M' is a transition metal or a group 13 metal. In some embodiments, M' is selected from the group consisting of aluminum, chromium, indium and gallium. In some embodiments, M' is aluminum.

In some embodiments, M' is chromium. In some embodiments, the Lewis acid includes a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand.

DEFINITIONS

Figure 1:
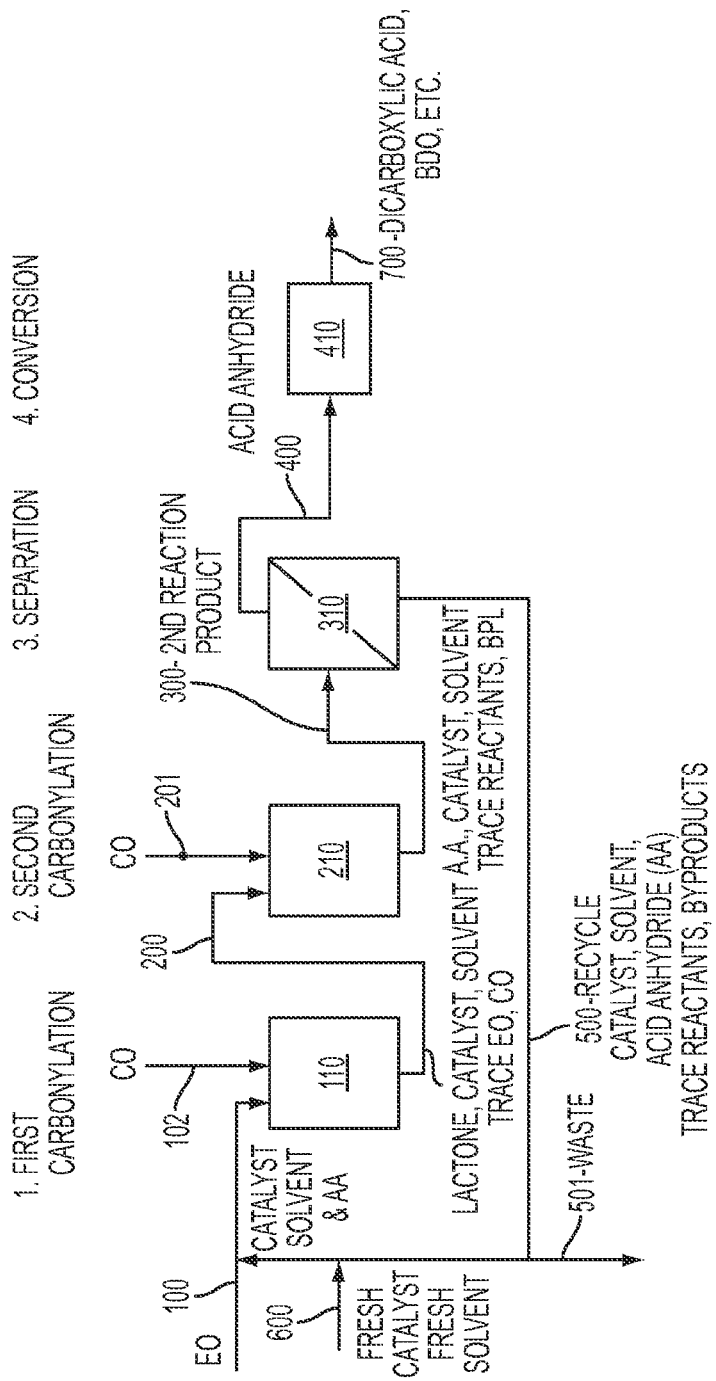
FIG. 1 shows a process flow diagram of an exemplary reaction system.
Figure 2:
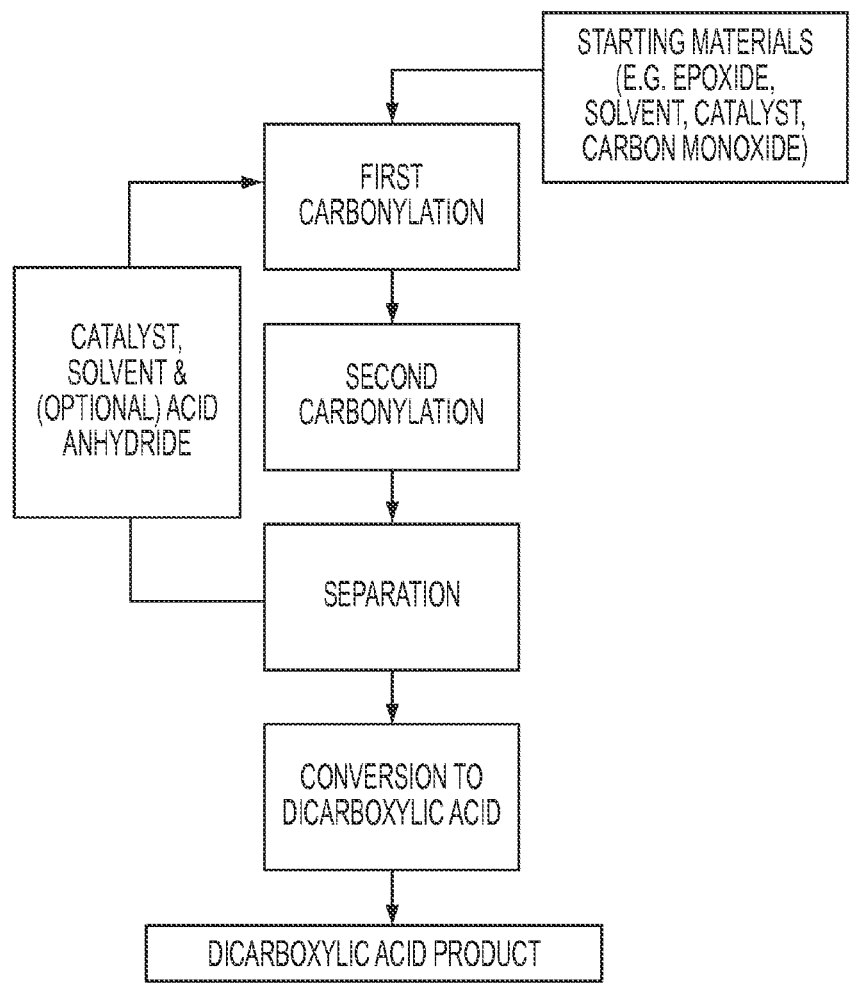
FIG. 2 shows a flow chart of exemplary reaction and process steps.
Figure 3:
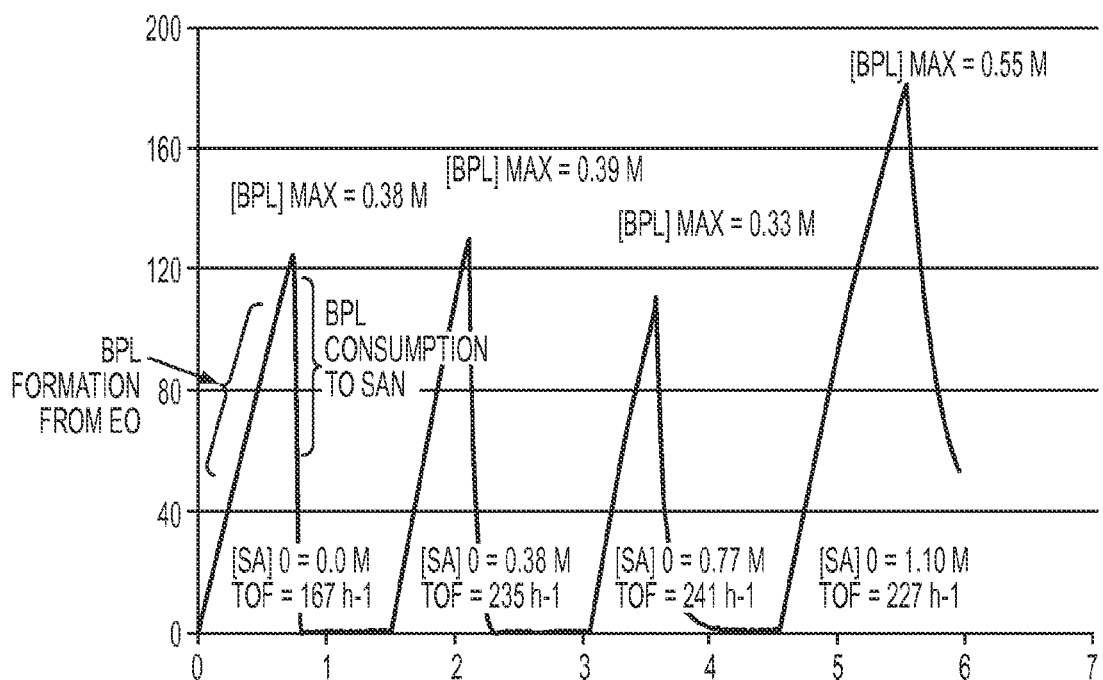
FIG. 3 shows a graph of the concentration of β-propiolactone during carbonylation of successive additions of ethylene oxide to a carbonylation reaction. The concentration of β-propiolactone increases with each addition of ethylene oxide, but rapidly decreases once all ethylene oxide is converted to β-propiolactone, as the β-propiolactone is converted to succinic anhydride.
Figure 4:
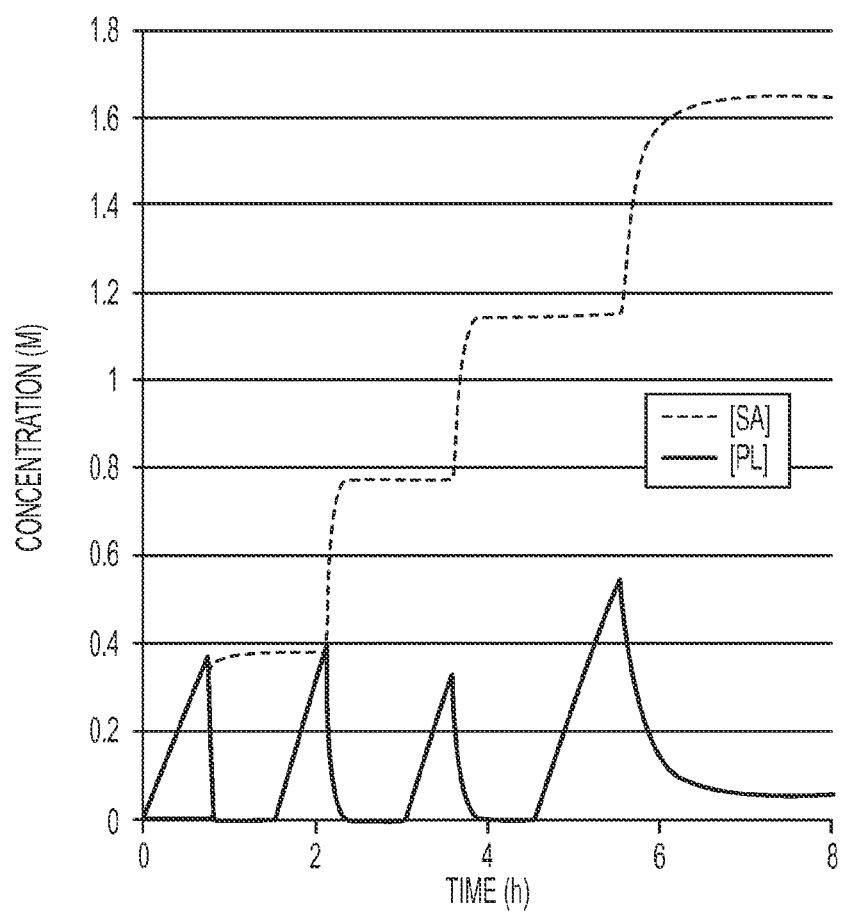
FIG. 4 shows a graph of β-propiolactone and total succinic anhydride concentration during the same exemplary reaction. The concentration of succinic anhydride appears to have little or no effect on the carbonylation of ethylene oxide to β-propiolactone and the subsequent further carbonylation of β-propiolactone to succinic anhydride.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

The terms "halo" and "halogen" as used herein refer to an atom selected from fluorine (fluoro, —F), chlorine (chloro, —Cl), bromine (bromo, —Br), and iodine (iodo, —I). The term "halogenic" as used herein refers to a compound substituted with one or more halogen atoms.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate. Because it is known that cylcopropane groups can in certain instances behave very much like double bonds, cyclopropane esters are specifically included within the definition of acrylate herein.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. The terms "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring.

Representative carbocyles include cyclopropane, cyclobutane, cyclopentane, cyclohexane, bicyclo[2,2,1]heptane, norbornene, phenyl, cyclohexene, naphthalene, spiro[4.5]decane, The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_{6-10}$ aryl" refer to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 pi electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1, 4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 14-membered heteroaryl" refers to a 5- to 6-membered heteroaryl ring having 1 to 3 heteroatoms independently selected from nitrogen, oxygen, or sulfur, or an 8- to 14-membered polycyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated, partially unsaturated, or aromatic and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}$Ph, which may be substituted with $R^\circ$; —$(CH_2)_{0-4}O(CH_2)_{0-1}$Ph which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NRO_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ)_2$; or —$(C_{1-4}$ straight or branched)alkylene)C(O)O—$N(R^\circ)_2$, wherein each $R^\circ$ may be substituted as defined below and is independently hydrogen, $C_{1-8}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-4}C(O)N(R^\circ)_2$; —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, —O(C(R*_2))_{2-3}O—, or —S(C(R*_2))_{2-3}S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*_2)_{2-3}O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, —(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate of a chemical reaction, while not being consumed or undergoing a permanent chemical change itself.

DETAILED DESCRIPTION OF VARIOUS EMBODIMENTS OF THE INVENTION

The present invention encompasses methods for the continuous production of acid anhydrides from an epoxide feedstock. Among other things, the present invention encompasses the inventor's discovery that the carbonylation of an epoxide to form beta lactone can be successfully performed in the presence of unexpectedly high concentrations of acid anhydride. This discovery enables new and efficient strategies for implementing continuous flow processes to convert epoxides to acid anhydrides.

In various aspects, the invention encompasses methods of a two step carbonylation 1 and 2 of epoxide compounds (e.g., ethylene oxide) to yield a beta-lactone (e.g., beta-propiolactone) after the first carbonylation 1 and an acid anhydride (e.g. succinic anhydride) after the second carbonylation 2. In some embodiments, the double carbonylation reactions described are performed in two separate reaction zones or vessels. This is largely because the first carbonylation reaction proceeds at a much slower rate as compared to the second carbonylation reaction. Additionally, the kinetics of the second carbonylation reaction 2 will not allow the second carbonylation to begin until substantially all epoxide is consumed. Thus, a continuous feed of epoxide to a single reactor results only in the intermediate lactone product being formed, as opposed to the ultimate reaction product, an acid anhydride.

With reference to FIG. 1, in various aspects, the product of the first carbonylation reaction 1 is a first reaction product stream 200. In various aspects, the product of the second carbonylation reaction 2 is a second reaction product stream 300. The acid anhydride is further separated 3 or isolated from the other components of the second reaction product stream 300. The acid anhydride can be further transformed to compounds including, but not limited to dicarboxylic acids (e.g., succinic acid), diols (e.g. 1,4 butanediol) and cyclic ethers (e.g THF). In some embodiments, either carbonylation reaction 1 or 2, or both is performed in the presence of a catalyst. In some embodiments, the epoxide is reacted with carbon monoxide at each step. In some embodiments, the catalyst is present in a solvent. Scheme 1 below illustrates the reaction sequence in one embodiment of the invention.

Scheme 1

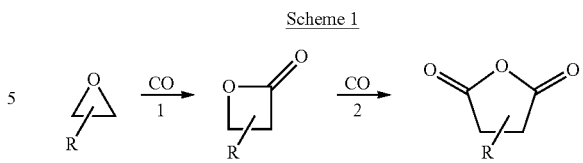

Carbonylation

First Carbonylation

With reference to FIG. 1, the first carbonylation step is performed by contacting a feed stream 100 comprising epoxide and optionally a carbonylation catalyst with carbon monoxide to provide a first reaction product stream 200 containing a first carbonylation product formed from the epoxide. In some embodiments, the first carbonylation reaction 1 is performed in the presence of a catalyst. In some embodiments, the first carbonylation reaction 1 is performed in a solvent. In some embodiments, the first carbonylation reaction is performed in a solution containing a substantial amount of dissolved acid anhydride. In some embodiments, the first carbonylation reaction is performed in a solution saturated with acid anhydride.

Reactants

Turning first to the first carbonylation reaction, the reactants may include various epoxides, including ethylene oxide, propylene oxide, or any of the other epoxides mentioned in the classes and subclasses herein either singly or in combination.

In certain embodiments, the epoxide starting material has formula I

(I)

where, $R^1$ and $R^2$ are each independently selected from the group consisting of: —H; optionally substituted $C_{1-6}$ aliphatic; optionally substituted phenyl; optionally substituted $C_{1-6}$ heteroaliphatic; optionally substituted 3- to 6-membered carbocycle; and optionally substituted 3- to 6-membered heterocycle, where $R^1$ and $R^2$ can optionally be taken together with intervening atoms to form a 3- to 6-membered, substituted or unsubstituted saturated or unsaturated ring optionally containing one or more heteroatoms.

In some embodiments, $R^1$ is hydrogen. In some embodiments, $R^1$ is phenyl. In some embodiments, $R^1$ is optionally substituted $C_{1-6}$ aliphatic. In some embodiments, $R^1$ is n-butyl. In some embodiments, $R^1$ is n-propyl. In some embodiments, $R^1$ is ethyl. In some embodiments, $R^1$ is —CF$_3$. In some embodiments, $R^1$ is —CH$_2$Cl. In other embodiments, $R^1$ is methyl.

In some embodiments, $R^2$ is hydrogen. In some embodiments, $R^2$ is optionally substituted $C_{1-6}$ aliphatic. In some embodiments, $R^2$ is methyl.

In certain embodiments, $R^1$ and $R^2$ are taken together with intervening atoms to form a 3- to 6-membered, substituted or unsubstituted ring optionally containing one or more heteroatoms. In some embodiments, $R^1$ and $R^2$ are taken together with intervening atoms to form a cyclopentyl or cyclohexyl ring.

In certain embodiments, an epoxide is chosen from the group consisting of: ethylene oxide, propylene oxide, 1,2- butylene oxide, 2,3-butylene oxide, epichlorohydrin, cyclohexene oxide, cyclopentene oxide, 3,3,3-Trifluoro-1,2-epoxypropane, styrene oxide, a glycidyl ether, and a glycidyl ester.

In certain embodiments, the epoxide is ethylene oxide.
In certain embodiments, the epoxide is propylene oxide.
In certain embodiments, the first carbonylation reaction 1 comprises the reaction shown in Scheme 2:

Scheme 2

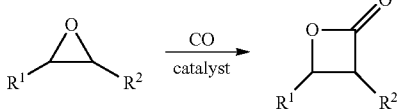

where each of $R^1$ and $R^2$ is as defined above and described in classes and subclasses herein.

In certain embodiments, the first carbonylation reaction 1 comprises the reaction shown in Scheme 3:

Scheme 3

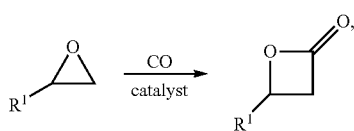

where $R^1$ is selected from the group consisting of —H and $C_{1-6}$ aliphatic.

In certain embodiments, the first carbonylation reaction 1 comprises the reaction shown in Scheme 4:

Scheme 4

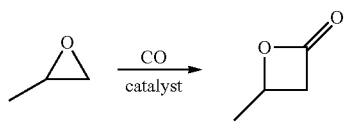

In certain embodiments, the first carbonylation reaction 1 comprises the reaction shown in Scheme 5:

Scheme 5

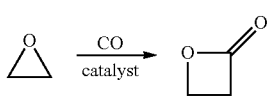

The methods include carbon monoxide, or a mixture of carbon monoxide and another gas. In some embodiments, carbon monoxide is provided in a mixture with hydrogen (e.g., Syngas). The ratio of carbon monoxide and hydrogen can be any ratio from 1:20 to 20:1, particularly from 1:10 to 10:1 or from 1:4 to 4:1, including but not limited to 1:1, 1:2, 1:4, 1:10, 10:1, 4:1, or 2:1. In some embodiments, the carbon monoxide is provided in a mixture containing other gases. The carbon monoxide sources include but are not limited to: syngas, wood gas, producer gas, coal gas, town gas, manufactured gas, hygas, Dowson gas or water gas, among others. In some embodiments, the carbon monoxide is provided by steam reforming from a hydrocarbon (e.g., methane). The carbon monoxide can be purified by pressure swing absorption to reduce the quantity of other gases in the steam reforming effluent. In some embodiments, the carbon monoxide is provided at super-atmospheric pressure. The quantity of carbon monoxide should be supplied to effect efficient conversion of the epoxide starting material to a beta-lactone.

Second Carbonylation

With reference to FIG. 1, the second carbonylation step is performed contacting a first reaction product stream 200, and optionally a carbonylation catalyst with carbon monoxide to provide a second reaction product stream 300 containing a second carbonylation product formed from the beta-lactone. In some embodiments, the second carbonylation reaction 2 is performed in the presence of a catalyst. In some embodiments, the second carbonylation reaction 2 is performed in a solvent. In some embodiments, the second carbonylation reaction 2 is performed in a solution saturated with acid anhydride.

Reactants

Turning now to the second carbonylation reaction 2, the reactants may include various lactones, produced from the first carbonylation reaction, including beta-propiolactone. The second carbonylation product may include various acid anhydrides, including succinic anhydride. In some embodiments, the second carbonylation reaction 2 does not commence until substantially all epoxide feed stock is converted to a lactone.

In certain embodiments, the lactone starting material has formula II:

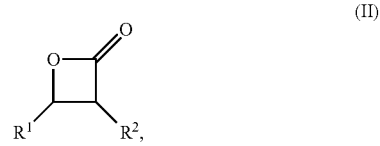

(II)

where, $R^1$ and $R^2$ are each independently selected from the group consisting of: —H; optionally substituted $C_{1-6}$ aliphatic; optionally substituted phenyl; optionally substituted $C_{1-6}$ heteroaliphatic; optionally substituted 3- to 6-membered carbocycle; and optionally substituted 3- to 6-membered heterocycle, where $R^1$ and $R^2$ can optionally be taken together with intervening atoms to form a 3- to 6-membered, substituted or unsubstituted saturated or unsaturated ring optionally containing one or more heteroatoms.

In some embodiments, $R^1$ is hydrogen. In some embodiments, $R^1$ is phenyl. In some embodiments, $R^1$ is optionally substituted $C_{1-6}$ aliphatic. In some embodiments, $R^1$ is n-butyl. In some embodiments, $R^1$ is n-propyl. In some embodiments, $R^1$ is ethyl. In some embodiments, $R^1$ is —$CF_3$. In some embodiments, $R^1$ is —$CH_2Cl$. In other embodiments, $R^1$ is methyl.

In some embodiments, $R^2$ is hydrogen. In some embodiments, $R^2$ is optionally substituted $C_{1-6}$ aliphatic. In some embodiments, $R^2$ is methyl.

In certain embodiments, $R^1$ and $R^2$ are taken together with intervening atoms to form a 3- to 6-membered, substituted or unsubstituted ring optionally containing one or more heteroatoms. In some embodiments, $R^1$ and $R^2$ are taken together with intervening atoms to form a cyclopentyl or cyclohexyl ring.

In some embodiments, a lactone is chosen from the group consisting of: acetolactones, propiolactones, butyrolactones, and valerolactones.

In some embodiments, the lactone is beta-propiolactone.

In certain embodiments, the second carbonylation reaction 2 comprises the reaction shown in Scheme 6:

Scheme 6

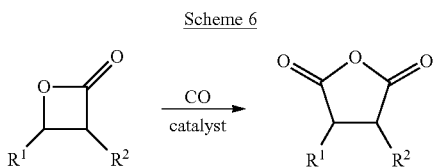

In certain embodiments, the second carbonylation reaction 2 comprises the reaction shown in Scheme 7:

Scheme 7

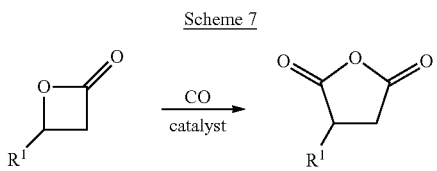

In certain embodiments, the second carbonylation reaction 2 comprises the reaction shown in Scheme 8:

Scheme 8

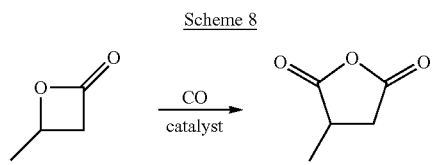

In certain embodiments, the second carbonylation reaction 2 comprises the reaction shown in Scheme 9:

Scheme 9

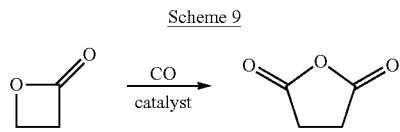

Similar to the first carbonylation reaction 1, the second carbonylation reaction 2 can include additional carbon monoxide, and/or a mixture of carbon monoxide and other gases. In some embodiments, carbon monoxide is provided in a mixture with hydrogen (e.g., Syngas). The ratio of carbon monoxide and hydrogen can be any ratio from 1:20 to 20:1, particularly from 1:10 to 10:1 or from 1:4 to 4:1, including but not limited to 1:1, 1:2, 1:4, 1:10, 10:1, 4:1, or 2:1. In some embodiments, the carbon monoxide is provided in a mixture containing other gases. The carbon monoxide sources include but are not limited to: wood gas, producer gas, coal gas, town gas, manufactured gas, hygas, Dowson gas or water gas, among others. In some embodiments, the carbon monoxide is provided at super-atmospheric pressure. The quantity of carbon monoxide should be supplied to effect efficient conversion of the lactone starting material to an acid anhydride.

Catalyst

In certain embodiments, a carbonylation catalyst comprises a metal carbonyl complex. In some embodiments, a metal carbonyl complex has the general formula $[QM_y(CO)_w]^x$, where:

Q is any suitable ligand and need not be present;

M is a metal atom;

y is an integer from 1 to 6 inclusive;

w is a number such as to provide the stable metal carbonyl; and x is an integer from −3 to +3 inclusive.

In certain embodiments where a metal carbonyl complex has the formula $[QM_y(CO)_w]^x$, M is selected from the group consisting of Ti, Cr, Mn, Fe, Ru, Co, Rh, Ni, Pd, Cu, Zn, Al, Ga and In. In certain embodiments, M is Co. In certain embodiments, a metal carbonyl complex is $Co(CO)_4^-$.

In certain embodiments, a carbonylation catalyst further comprises a Lewis acidic component. In certain embodiments, a Lewis acidic component is cationic. In some embodiments, a carbonylation catalyst comprises an anionic metal carbonyl complex (e.g. x is a negative integer) and a cationic Lewis acidic component. In certain embodiments, the metal carbonyl complex comprises a carbonyl cobaltate and the Lewis acidic component comprises a metal-centered cationic Lewis acid.

In certain embodiments, a metal-centered cationic Lewis acid is a metal complex of formula $[M'(L)_b]^{c+}$, where:

M' is a metal;

each L is a suitable ligand;

b is an integer from 1 to 6 inclusive;

c is 1, 2, or 3; and where, if more than one L is present, each L may be the same or different.

In some embodiments where a metal-centered Lewis acid is a metal complex of formula $[M'(L)_b]^{c+}$, M' is selected from the group consisting of: a transition metal, a group 13 or 14 metal, and a lanthanide. In certain embodiments, M' is a transition metal or a group 13 metal. In certain embodiments, M' is selected from the group consisting of aluminum, chromium, indium and gallium. In certain embodiments, M' is aluminum. In certain embodiments, M' is chromium. In certain embodiments, M' is cobalt.

In certain embodiments, a metal-centered Lewis-acidic component of a carbonylation catalyst includes a dianionic tetradentate ligand. A large number of such ligands are known in the art, and the present invention is not intended to be limited to the specific ligands mentioned herein. The preparation, modification and evaluation of such ligands, as well as their analogs, derivatives and complexes are well known to the skilled artisan and it is to be understood that the methods taught herein may be deployed with variations in the ligand of the Lewis acidic metal complex. The choice of ligand is impacted by factors such as the cost of the ligand, the solubility of the complex, the chemical stability of the ligand under the reaction conditions, the reaction rate and selectivity of the catalytic process using the ligand, and the productivity and lifetime of the catalyst in the desired process. The optimization of such variables based on the teachings and disclosure herein is a matter of routine experimentation.

In certain embodiments, a dianionic tetradentate ligand is selected from the group consisting of: porphyrin, substituted porphyrin, salen, substituted salen, salcy, substituted salcy, salph, substituted salph, salan, substituted salan, dibenzotetramethyltetraaza[14]annulene ("TMTAA"), substituted TMTAA, phthalocyaninate, substituted phthalocyaninate, the Trost ligand, and substituted Trost ligand.

In some embodiments, a dianionic tetradentate ligand is porphyrin. In some embodiments, a dianionic tetradentate ligand is a substituted porphyrin. In some embodiments, a dianionic tetradentate ligand is ClTPP (meso-tetra(4-chlorophenyl)porphyrin). In some embodiments, a dianionic tetradentate ligand is TPP (tetraphenylporphyrin). In some embodiments, a dianionic tetradentate ligand is OEP (octaethylporphyrin). In some embodiments, a dianionic tetradentate ligand is a salen (N,N'-ethylenebis(salicylimine) ligand. In some embodiments, a dianionic tetradentate ligand is a salph (N,N'-bis(salicylidene)-o-phenylenediamine) ligand. In some embodiments, a dianionic tetradentate ligand is a salcy (N,N'-bis(3,5-di-tert-butylsalicylidene)-1,2-diaminocyclohexane) ligand.

In certain embodiments, a carbonylation catalyst comprises a carbonyl cobaltate in combination with an aluminum porphyrin compound as a Lewis-acidic component. In some embodiments, a carbonylation catalyst comprises [(TPP)Al][Co(CO)$_4$]. In some embodiments, a carbonylation catalyst comprises [(ClTPP)Al][Co(CO)$_4$]. In some embodiments, a carbonylation catalyst comprises [(OEP)Al][Co(CO)$_4$]. In some embodiments, a carbonylation catalyst comprises [(porphyrin)Al][Co(CO)$_4$].

In certain embodiments, a carbonylation catalyst comprises a carbonyl cobaltate in combination with a chromium porphyrin compound as a Lewis-acidic component.

In certain embodiments, a carbonylation catalyst comprises a carbonyl cobaltate in combination with a chromium salen compound as a Lewis-acidic component. In some embodiments, a carbonylation catalyst comprises [(salcy)Cr][Co(CO)$_4$].

In certain embodiments, a carbonylation catalyst comprises a carbonyl cobaltate in combination with a chromium salophen compound as a Lewis-acidic component. In some embodiments, a carbonylation catalyst comprises [(salph)Cr][Co(CO)$_4$].

In certain embodiments, a carbonylation catalyst comprises a carbonyl cobaltate in combination with an aluminum salen compound as a Lewis-acidic component. In certain embodiments, a carbonylation catalyst comprises a carbonyl cobaltate in combination with an aluminum salophen compound as a Lewis-acidic component. In certain embodiments, a carbonylation catalyst comprises a carbonyl cobaltate in combination with a substituted aluminum salophen compound as a Lewis-acidic component. In some embodiments, a carbonylation catalyst comprises [(salph)Al][Co(CO)$_4$]. In some embodiments, a carbonylation catalyst comprises [(salcy)Al][Co(CO)$_4$].

In certain embodiments, a carbonylation catalyst comprises a carbonyl cobaltate in combination with an chromium porphyrin compound as a Lewis-acidic component. In some embodiments, a carbonylation catalyst comprises [(TPP)Cr][Co(CO)$_4$]. In some embodiments, a carbonylation catalyst comprises [(ClTPP)Cr][Co(CO)$_4$]. In some embodiments, a carbonylation catalyst comprises [(OEP)Cr][Co(CO)$_4$]. In some embodiments, a carbonylation catalyst comprises [(porphyrin)Cr][Co(CO)$_4$].

In certain embodiments, a carbonylation catalyst further comprises one or more electron donating groups. In certain embodiments, such electron donating groups are solvent molecules. In some embodiments, an electron donating group is a solvent molecule in which the catalyst, or a portion thereof, was synthesized. In certain embodiments, an electron donating group is an ether. In certain embodiments, an electron donating group is THF. In certain embodiments, an electron donating group is 1,4-dioxane.

In some embodiments, each carbonylation reaction uses a different carbonylation catalyst. In such embodiments the reaction system may include an intermediate step between the carbonylation reactions in which the first carbonylation catalyst is removed. In such embodiments the reaction system may include an intermediate step between the carbonylation reactions in which the second carbonylation catalyst is added.

In some embodiments, the first carbonylation reaction proceeds with both carbonylation catalysts present in the reaction. In some embodiments, the second carbonylation reaction proceeds with both carbonylation catalysts present in the reaction.

Solvents

With respect to solvents (i.e., reaction solvents), methods of the invention have been found to be improved by the presence of a solvent. In some embodiments, solvents are of a low to moderate polarity. In some embodiments, the solvent fully dissolves the epoxide to provide a reaction mixture in which the catalyst employed is at least partially soluble. Additionally, in certain embodiments, the solvents lack reactive functional groups (e.g. amines, alcohols, acidic hydrogen atoms, basic nitrogen atoms and the like).

In some embodiments, the solvent includes a Lewis base. The term Lewis base as used herein refers to any nucleophilic species that is capable of donating an electron pair, examples include oxygen atoms (e.g. ethers, ketones, esters, carbonates and the like), amides, nitriles, phosphines and the like. In some embodiments, the presence of suitable solvents can suppress the formation of polymeric side products and, in some cases, increase the rate and/or yield of the reaction.

In certain embodiments, the Lewis base is distinct from the epoxide. In other embodiments, the Lewis base is the epoxide (i.e., the reaction is performed in neat epoxide). Indeed, while the use of non-epoxide solvents may lead to higher yields, we have found that certain catalysts allow double carbonylation to be achieved in neat epoxide.

In certain embodiments, the solvent used will fully dissolve the epoxide and provide a reaction mixture in which the catalyst employed is at least partially soluble. Suitable solvents may include ethers, ketones, aromatic hydrocarbons, halocarbons, esters, nitriles, and some alcohols. For example, without limitation, a suitable solvent may include: 1,4-dioxane; 1,3-dioxane; tetrahydrofuran; tetrahydropyran; dimethoxyethane; glyme; diethyl ether; t-butyl methyl ether; 2,5-dimethyl tetrahydrofuran; ethyl acetate; propyl acetate; butyl acetate; acetone; 2-butanone; cyclohexanone; toluene; acetonitrile; and difluorobenzene. In some embodiments, the solvent includes 1,4-dioxane, toluene, and/or dimethoxyethane. In one embodiment, solvent includes 1,4-dioxane. Mixtures of two or more of the above solvents are also useful, and in some cases may be preferred to a single solvent. For example, mixtures of toluene and 1,4-dioxane are useful.

In certain embodiments, we have found that Lewis bases of low to moderate polarity (as determined by dielectric constant at 20° C.) improve the performance of the reaction over polar solvents. Thus, in certain embodiments, the solvent may include a Lewis base which is less polar than 1,3-dioxane ($\in$=dielectric constant at 20° C.=13.6). In certain embodiments, the solvent includes a Lewis base which is less polar than ortho-difluorobenzene ($\in$=13). In certain embodiments, the solvent includes a Lewis base which is less polar than meta-difluorobenzene ($\in$=5). In certain embodiments, the solvent includes a Lewis base with substantially the same polarity as 1,4-dioxane ($\in$=2.2). In certain embodiments, the solvent includes a Lewis base with a polarity ($\in$) between about 1 and about 4. In certain embodiments, the solvent includes a Lewis base with a polarity ($\in$) between about 1.5 and about 3.5. In certain embodiments, the solvent includes a Lewis base with a polarity ($\in$) between about 2 and about 3. In certain embodiments, the solvent includes a Lewis base with a polarity ($\in$) of about 2. In certain embodiments, the solvent includes a Lewis base with a polarity ($\in$) of about 2 to 2.4.

In certain embodiments, we have found that Lewis bases of low to moderate electron donicity improve the performance of the reaction over strongly donating Lewis bases. Thus, in certain embodiments, the solvent may include a Lewis base with lower electron donicity than tetrahydrofuran. In certain embodiments, the solvent may include a Lewis base with lower electron donicity than 2-methyltetrahydrofuran. In certain embodiments, the solvent may include a Lewis base with lower electron donicity than 2,5-dimethyltetrahydrofuran. In certain embodiments, the solvent may include a Lewis base with higher electron donicity than difluorobenzene. In certain embodiments, the solvent may include a Lewis base with higher electron donicity than toluene. In certain embodiments, the solvent may include a Lewis base with substantially the same electron donicity as 1,4-dioxane.

It will be appreciated that while 1,4-dioxane appears to produce particularly high yields of anhydride when used in combination with various catalysts that are described in the Examples, other solvents and mixtures of solvents (including solvents and mixtures that are not explicitly disclosed) may be used with these catalysts. While some of these combinations may produce lower yields they remain within the scope of the present invention. It will also be appreciated that present invention is in no way limited to the representative catalysts that are exemplified in this application. In particular, now that we have demonstrated that high yield double carbonylation is possible through appropriate selection of catalyst and solvent, those skilled in the art will recognize that our teachings can be generalized to other catalyst/solvent combinations.

In general, highly polar, reactive or protic solvents are inferior or unsuitable for processes of the present invention. Inferior solvents include ionic liquids, chlorinated hydrocarbons, sulfolane, dimethylsulfoxide, formamide, pyridine, and the like.

The solvent is preferably added in an amount sufficient to achieve an epoxide concentration of from about 0.1M to about 20M, for example from about 0.1M to about 5M or from about 0.5M to about 2M.

Reaction Conditions

The conditions for each carbonylation reaction are independently selected based on a number of factors to effect conversion of the epoxide to a beta-lactone and the conversion of the beta-lactone to an acid anhydride. Temperature, pressure, and reaction time influence reaction speed and efficiency. Additionally, the ratio of reactants to each other and to the catalyst effect reaction speed and efficiency. In some embodiments, the conditions between the two reactions are identical. In some embodiments the conditions between the two reactions are different.

In some embodiments, either reaction temperature can, independently, range from between about −20° C., to about 600° C. In some embodiments, the reaction temperature is about −20° C., about 0° C., about 20° C., about 40° C., about 60° C., about 80° C., about 100° C., about 200° C., about 300° C., about 400° C., about 500° C. or about 600° C. In some embodiments, the reactants, catalyst and solvent are supplied to the reactor at standard temperature, and then heated in the reactor. In some embodiments, the reactants are pre-heated before entering the reactor. In some embodiments, the reactants are cooled before entering the reactor.

Turning to the effect of temperature, in certain embodiments the reaction temperature was found to affect the rate and outcome of processes of the invention. At higher temperatures the reaction proceeds more quickly than at lower temperatures, but the propensity to form reaction by-products may increase.

In some embodiments, the reaction pressure can range from between about 50 psig to about 5000 psig. In some embodiments, the reaction pressure is about 100 psig, about 200 psig, about 300 psig, about 400 psig, about 500 psig, about 600 psig, about 700 psig, about 800 psig, about 900 psig, or about 1000 psig. In some embodiments, the pressure ranges from about 50 psig to about 2000 psig. In some embodiments, the pressure ranges from about 100 psig to 1000 psig. In some embodiments, the pressure ranges from about 200 psig to about 800 psig. In some embodiments, the pressure ranges from about 1000 psig to about 5000 psig. In some embodiments, the pressure ranges from about 1000 psig to about 3000 psig. In some embodiments, the pressure ranges from about 3000 psig to about 5000 psig. In some embodiments, the reaction pressure is supplied entirely by the carbon monoxide. For example, the reactants, catalyst and solvent are charged to the reactor at atmospheric pressure, or under a vacuum, and carbon monoxide is added to the reactor to increase pressure to the reaction pressure. In some embodiments, all reactants, solvent and catalyst are supplied to the reactor at reaction pressure.

Optionally, the atmosphere under which the reaction is conducted can include other gasses. Such other gasses can include, for example, hydrogen, methane, nitrogen, carbon dioxide, air, and trace amounts of steam. The present invention also specifically encompasses processes in which other carbon monoxide-containing gas streams provide the atmosphere under which the reaction is conducted, as described above. Undesirable side-product can be minimized at higher reaction temperatures by performing the reaction at relatively high carbon monoxide pressures. In some cases therefore, the optimal temperature will be dependent upon the pressure at which the reaction is conducted. At high carbon monoxide pressures, e.g., greater than about 400 psi, elevated temperatures were found to be advantageous for the reaction (e.g., up to about 120° C.). In some cases, the reaction may be conducted at a temperature ranging from about 40° C. to about 80° C. To avoid by-product formation, the reaction mixture may be pressurized with CO while at a low temperature (e.g., <0° C.) and heating is introduced only after CO has been allowed to contact the reaction mixture. If minimization of by-product is desired, the CO pressure may be applied for a period of time prior to heating the mixture (e.g., at least 5 minutes prior to heating).

In some embodiments, the ratio of catalyst to epoxide or lactone is selected, based on other reaction conditions, so that the reaction proceeds in an economical and time-feasible manner. In some embodiments, the ratio of catalyst to epoxide is ranges from about 1:10000 to about 1:5, from about 1:5000 to about 1:10, or from about 1:1000 to about 1:100 on a molar basis. In some embodiments, the ratio of catalyst to epoxide is about 1:10000 on a molar basis. In some embodiments, the molar ratio of catalyst to epoxide is about 1:5000, is about 1:2500, is about 1:2000, is about 1:1500, is about 1:1000, is about 1:750, is about 1:500, is about 1:250, is about 1:200, is about 1:150, or is about 1:100. In some embodiments, the concentration of the epoxide is in the range between about 0.1 M and about 5.0 M. In some embodiments, the concentration of the epoxide is in the range between about 0.5 M and about 3.0 M.

In some embodiments, the catalyst is preferably present in an amount sufficient to allow the reaction process to be completed in a convenient time interval (e.g. less than about 24 hours, for example less than about 3 hours). In real terms this can require catalyst loadings ranging from about 0.0001 mole percent to about 20 mole percent based on the epoxide substrate. In certain embodiments, the catalyst loading can range from about 0.0001 mole percent to about 1 mole percent, e.g., from about 0.0001 mole percent to about 0.1 mole percent or from about 0.0001 mole percent to about 0.01 mole percent. In certain embodiments, the catalyst loading can range from about 0.001 mole percent to about 20 mole percent, e.g., from about 0.1 mole percent to about 1 mole percent or from about 0.067 mole percent to about 5 mole percent. In some embodiments, the catalyst loading is less than about 0.154 mole percent based on the epoxide substrate. In one such embodiment, the epoxide is ethylene oxide.

In some embodiments, the first carbonylation reaction 1 is maintained for a period of time sufficient to allow complete, near complete reaction of the epoxide to beta-lactone or as complete as possible based on the reaction kinetics and or reaction conditions. In some embodiments, the reaction time is maintained for about 12 hours, about 8 hours, about 6 hours, about 3 hours, about 2 hours, about 1 hour, about 0.5 hours, about 10 minutes, about 5 minutes or about 1 minute. In some embodiments, the reaction time is established as a residence time within the first carbonylation reactor 110. The reaction can be halted by reducing the reactor temperature or pressure, withdrawing a particular reactant or introducing a quenching compound. The reaction may be halted at any point or any percentage conversion of epoxide to beta-lactone. E.g., the reaction may be halted when 50% of the epoxide is converted to beta-lactone, or when the supply of epoxide is exhausted to nearly entirely converted to a beta-lactone.

In certain embodiments, where the first carbonylation reaction 1 is performed under steady state conditions, the reactor is fed and maintained under reaction conditions such that the fed epoxide has a residence time in the reactor sufficient to allow complete, or near complete reaction of the epoxide to beta-lactone. In some embodiments, the residence time is about 12 hours, about 8 hours, about 6 hours, about 3 hours, about 2 hours, about 1 hour, about 0.5 hours, about 10 minutes, about 5 minutes or about 1 minute.

In some embodiments, the second carbonylation reaction 2 is maintained for a period of time sufficient to allow complete, near complete reaction of the beta-lactone to acid anhydride or as complete as possible based on the reaction kinetics and or reaction conditions. In some embodiments, the reaction time is maintained for about 12 hours, about 8 hours, about 6 hours, about 3 hours, about 2 hours, about 1 hour, about 0.5 hours, about 10 minutes, about 5 minutes or about 1 minute. In some embodiments, the reaction time is established as a residence time within the second carbonylation reactor 210. The reaction can be halted by reducing the reactor temperature or pressure, withdrawing a particular reactant or introducing a quenching compound. The reaction may be halted at any point or any percentage conversion of beta-lactone to acid anhydride. E.g., the reaction may be halted when 50% of the beta-lactone is converted to acid anhydride or the beta lactone is exhausted.

Carbonylation Reaction Products

As described above, the first reaction product of the first carbonylation reaction 1 is a beta-lactone (e.g., beta-propiolactone, beta-butyrolactone). Additionally, the reaction product stream 200 may contain other reaction by-products, un-reacted reactants, as well as catalyst and solvent. In some embodiments, the un-reacted reactants include epoxide or carbon monoxide. As such, the reaction may not proceed to completion and may be considered a partial reaction.

In some embodiments, in the first carbonylation reaction 1, the amount of un-reacted epoxide is sufficient to prevent the formation of an acid anhydride (e.g., succinic anhydride). Without being bound by a particular theory, it is speculated that the second carbonylation reaction 2, (e.g., converting the beta-propiolactone to succinic anhydride) does not proceed, unless substantially all of the epoxide is consumed. Thus a fraction of the epoxide feed to the first carbonylation reactor 110 that exits un-reacted appears to prevent the formation of succinic anhydride. In some embodiments, the first reaction product stream 200 contains less than about 5% epoxide, less than about 3% epoxide, less than about 1% epoxide or less than about 0.1%, by weight.

In some embodiments, by-product formation from first carbonylation reaction 1 includes the formation of one or more of the following compounds: crotonaldehyde, acrylic acid, 1,4 dioxane, acrylic acid dimers and trimers, 2-hydroxyethyl acrylate, 2,5 hexandienal, 3-oxacaprolactone, diethylene glycol monoacrylate, 3-hydroxypropionic acid, diethylene glycol diacrylate, 5-valeroactone and/or 2,6-dimethyl-1,3-dioxan-4-ol.

As described above, the second reaction product of the second carbonylation reaction 2 is an acid anhydride (e.g., succinic anhydride). Additionally, the second reaction product stream 300 may contain other reaction by-products, un-reacted reactants, as well as catalyst and solvent. In some embodiments, the un-reacted reactants include beta-lactone, epoxide or carbon monoxide. As such, the reaction may not proceed to completion and may be considered a partial reaction.

Reaction Mode

In some embodiments, the first carbonylation reaction 1 is performed in a continuous operation. Although the reaction vessels are referred to as a first reactor and a second reactor, it is contemplated that the two reactions take place in two different zones within the same reaction vessel. For example, a tubular or plug-flow reactor with two distinct reactions zones, within one continuous volume. The reactants are continuously fed to a first carbonylation reactor 110. In some embodiments, the first carbonylation reactor 110 is stirred, and in some embodiments, there is no mixing in the first carbonylation reactor 110. In some embodiments, the first carbonylation reactor 110 includes a gas-entrainment impeller. The reactants may be fed to the first carbonylation reactor 110 at standard temperature and/or pressure and then heated or pressurized to reaction conditions once in the first carbonylation reactor 110. The first carbonylation reactor 110 may itself be any reactor conducive to continuous operation, including by not limited to a continuously stirred tank reactor or a tubular reactor. In some embodiments, the first carbonylation reactor 110 is an adiabatic reactor, and/or an isothermal reactor. In some embodiments, the reactor pressure is constant. In some embodiments, the reactor pressure varies as the reaction progresses. In some embodiments, the reactor temperature varies as the reaction progress. In some embodiments, the reaction is performed in a batch operation. One of ordinary skill in the art will recognize the temperatures, pressures, catalyst ratios, concentrations of reactants, catalyst and solvents, flow rates can all be optimized or varied to achieve a given reaction outcome.

In some embodiments, the second carbonylation reaction 2 is performed in a continuous operation. The reactants are continuously fed to a second carbonylation reactor 210. In some embodiments, the second carbonylation reactor 210 is stirred, and in some embodiments, there is no mixing in the second carbonylation reactor 210. In some embodiments, the second carbonylation reactor 210 includes a gas-entrainment impeller. In some embodiments, the second carbonylation reactor 210 is a plug-flow reactor. The reactants, the first reaction product stream 200, may be fed to the second carbonylation reactor 210 at standard temperature and/or pressure and then heated or pressurized to reaction conditions once in the second carbonylation reactor 210. The reactants, the first reaction product stream 200, may be feed to the second carbonylation reactor 210 at temperature and pressure equal to the temperature and pressure of operation of the first carbonylation reaction 1. The reactants, the first reaction product stream 200, may be feed to the second carbonylation reactor 210 at temperature and pressure equal to the temperature and pressure of operation of the second carbonylation reaction 2. The reactants, the first reaction product stream 200, may be feed to the second carbonylation reactor 210 at any temperature between, above or below the first or second carbonylation reaction temperatures or pressures. In some embodiments, the addition of more carbon monoxide to the first reaction product stream 200 demarcates the beginning of the second carbonylation reaction 2, or the beginning of the second carbonylation reactor 210.

The second carbonylation reactor 210 itself may be any reactor conducive to continuous operation, including but not limited to a continuously stirred tank reactor or a tubular reactor (e.g., a plug-flow reactor). In some embodiments, the second carbonylation reactor 210 is an adiabatic reactor, and/or an isothermal reactor. In some embodiments, the reactor pressure is constant. In some embodiments, the reactor pressure varies as the reaction progresses. In some embodiments, the reactor temperature varies as the reaction progress. In some embodiments, the reaction is performed in a batch operation. One of ordinary skill in the art will recognize the temperatures, pressures, catalyst ratios, concentrations of reactants, catalyst and solvents, flow rates can all be optimized or varied to achieve a given reaction outcome.

In some embodiments, as described above, the various individual reaction products, or even the entire second reaction product stream 300 can be recycled to the first carbonylation reactor 110 or the feed stream 100 as a recycle stream 500. In some embodiments, the reaction products are separated into at least two streams, as described below. Generally, at least one stream will contain at least a substantial portion of the solvent and catalyst and the other stream will contain at least a substantial portion of the acid anhydride product. Either or both of these streams may be recycled to the outlet of the first carbonylation reaction 1 either with or without the separation step 3 being performed.

In some embodiments, the catalyst and/or solvent stream is recycled to the feed stream or to the first carbonylation reactor 110. In some embodiments, the portion of the solvent and/or catalyst from the second reaction product stream 300 recycled to the first carbonylation reactor 110 or feed stream 100 ranges from about 0% to about 100%. In some embodiments, a portion of the solvent and/or catalyst from the second reaction product stream 300 recycled to the first carbonylation reactor 110 or feed stream 100 is about 100%, about 90%, about 80%, about 70%, about 60%, about 50%, about 40%, about 30%, about 20%, about 10%, about 0%. In some embodiments, a different percentage of the catalyst, as compared to the solvent is recycled, i.e., the proportions of either the catalyst or solvent component do not need to be equal.

In some embodiments, a portion of the catalyst and/or solvent is withdrawn from the recycling stream 500 as a waste 510. The portion of the catalyst and/or solvent withdrawn as waste 510, as compared to the total catalyst and/or solvent in the first reaction product stream 200 may be in the range from about 0% to about 90%. The portion of the catalyst and/or solvent withdrawn as waste 510, as compared to the total catalyst and/or solvent in the first reaction product stream 200 may be about 90%, about 80%, about 70%, about 60, about 50%, about 40%, about 30%, about 20%, about 10%, about 5%, about 1%, about 0.5% or about 0.1%. The portion of the catalyst and/or solvent withdrawn as waste 510, as compared to the total catalyst and/or solvent in the first reaction product stream 200 may be less than 10%, less than 5%, less than 3%, less than 2%, less than 1%, less than 0.5%, less than 0.25%, or less than 0.1%.

In some embodiments, fresh catalyst and or solvent 600 is fed to either the recycling stream 500 or to the feed stream 100 in order to ensure that carbonylation reaction continues. The solvent and or catalyst added may make up for solvent and/or catalyst that is lost in the reaction, withdrawn as waste 510, entrained in the product stream, or exhausted and no longer useful. The portion of the catalyst and/or solvent added, as compared to the total catalyst and/or solvent in the reaction product stream may be in the range from about 0% to about 100%. The portion of the catalyst and/or solvent added, as compared to the total catalyst and/or solvent in the first reaction product stream 200 may be about 100%, about 90%, about 80%, about 70%, about 60, about 50%, about 40%, about 30%, about 20%, or about 10%.

In some embodiments, the second reaction product stream 300 is recycled to the first carbonylation reactor 110 or the reactant feed stream 100. As discussed below the acid anhydride product stream 400 is generally separated from second reaction product stream 300. In some embodiments the acid anhydride product stream 400 separated is from a portion of the second reaction product stream 300 and the remaining second reaction product stream 300 is recycled back to the feed stream 100 or the first carbonylation reactor 110. In some embodiments, the portion of second reaction product stream 300 recycled to the carbonylation reactor or feed stream ranges from about 0% to about 100%. In some embodiments, the portion acid anhydride from the second reaction product stream 300 recycled to the first carbonylation reactor 110 or feed stream 100 is about 100%, about 90%, about 80%, about 70%, about 60%, about 50%, about 40%, about 30%, about 20%, about 10%, about 0%. In some embodiments, 100% of the second reaction product stream 300 is recycled to the first carbonylation reactor 110 or feed stream 100, until the percentage of acid anhydride in either or both of the first or second reaction product streams 200 and 300 reaches a specified level. In some embodiments, the specified level ranges from about 5% to about 75%. In some embodiments, the specified level is about 5%, about 10%, about 20%, about 30%, about 40%, about 50%, about 60%, or about 75%. In some embodiments, that level is saturation of the acid anhydride in the feed stream 100, the first or second reaction product streams 200 or 300 at the given conditions of each stream or the first or second carbonylation reactor 110 and 210.

The carbonylation step may begin without any acid anhydride present in the first reaction product stream 200. After the start of the carbonylation, the acid anhydride produced from the carbonylation step may accumulate in the reaction second reaction product stream 300, and in some embodiments, the acid anhydride is not separated from the second reaction product stream 300 until the content of the acid anhydride in the second reaction product stream 300 reaches a threshold value. In certain embodiments, the threshold value is from about 5 to about 10% by weight. In certain embodiments, the threshold value is from about 10% to about 20% by weight. In certain embodiments, the threshold value is from about 20% to about 30% by weight. In certain embodiments, the threshold value is from about 30% to about 40% by weight. In certain embodiments, the threshold value is from about 40% to about 50% by weight. In certain embodiments, the threshold value is from about 50% to about 60% by weight. In certain embodiments, as described above, the threshold value is saturation of the acid anhydride in either reaction product stream 200 or 300 under the conditions of either the first or second carbonylation reaction 1 or 2.

Separation

In some embodiments, the present invention includes a separation step 3 of the acid anhydride product stream 400 from the second reaction product stream 300. The separation may be accomplished by a variety of separation means, including but not limited to solid-liquid, gas-liquid, and liquid-liquid separation techniques. In some embodiments, the portion of acid anhydride product stream 400 separated in the separation step 3 is between about 0% and about 100% of the second reaction product stream 300. As described above, the separation step 3 results in a recycle stream 500 comprising solvent, catalyst and/or acid anhydride and an acid anhydride stream 400 comprising the acid anhydride. In some embodiments, the separation results in all or nearly all of the reaction catalyst being retained in the recycle stream 500.

In some embodiments, the recycle stream 500 is treated before it is combined with the feed stream 100 or added to the first carbonylation reactor 110. Various treatments for the recycle stream 500 include, but are not limited to, filtration, heating, cooling, concentration, and any combinations of these. In some embodiments, epoxide is added to the recycle stream 500 before it is combined with the feed stream 100 or added to the first carbonylation reactor 110. In some embodiments, the catalyst is concentrated in the recycling stream 500. In some embodiments, the catalyst is concentrated to an extent that it precipitates in the recycling stream 500.

In some embodiments, the separation step 3 includes separating solid acid anhydride from the second reaction product stream 300. In some embodiments, the separation step 3 includes exposing the second reaction product stream 300 to conditions under which at least a portion of acid anhydride initially dissolved in the stream is no longer soluble. In some embodiments, this exposure includes lowering the temperature of the second reaction product stream 300, lowering the pressure of the second reaction product stream 300, and/or lowering the partial pressure of carbon monoxide in the second reaction product stream 300.

In some embodiments, the temperature of the second reaction product stream 300 is decreased by between about 1° C. and about 600° C. in the separation step 3. In some embodiments, the temperature of the second reaction product stream 300 is decreased by between about 5° C. and about 100° C., between about 10° C. and about 50° C., between about 20° C. and about 40° C., or between about 40° C. and about 80° C., in the separation step 3. In some embodiments, the temperature of the second reaction product stream 300 is decreased by about 1° C., about 2° C., about 3° C., about 4° C., about 5° C., about 10° C., about 15° C., about 20° C., about 40° C., about 60° C., about 80° C., about 100° C., about 200° C., about 300° C., about 400° C., about 500° C. or about 600° C. in the separation step 3.

In some embodiments, the temperature reduction of the second reaction product stream 300 is a decrease in temperature of between 1% and about 99% from the reaction temperature (on an absolute scale). In some embodiments, the temperature of the second reaction product stream 300 is about 1%, about 2%, about 5%, about 10%, about 20%, about 25%, about 30%, about 40%, about 50%, about 60%, about 75%, about 80%, about 90%, about 95% or about 99% from the temperature of the second carbonylation reaction 2.

In some embodiments, the pressure or the partial pressure of carbon monoxide of the second reaction product stream 300 is lowered by between about 1 psig and about 5000 psig in the separation step 3. In some embodiments, the total pressure or the partial pressure of carbon monoxide of the second reaction product stream 300 is lower by about 1 psig, about 5 psig, about 10 psig, about 20 psig, about 50 psig, about 75 psig, about 100 psig, about 200 psig, about 300 psig, about 400 psig, about 500 psig, about 600 psig, about 700 psig, about 800 psig, about 900 psig, about 1000 psig, about 2000 psig, about 3000 psig, about 4000 psig or about 5000 psig.

In some embodiments, the pressure (or partial pressure of carbon monoxide) reduction of the second reaction product stream 300 is a decrease in pressure (or partial pressure of CO) of between 1% and about 99.9% from the reaction pressure (or partial pressure of CO) (on an absolute scale). In some embodiments, the pressure of the second reaction product stream 300 is about 1%, about 2%, about 5%, about 10%, about 20%, about 25%, about 30%, about 40%, about 50%, about 60%, about 75%, about 80%, about 90%, about 95%, about 99%, about 99.5%, about 99.8% or about 99.9% from the second carbonylation reaction 2 pressure (or partial pressure of CO).

Solid-Liquid Separation

In some embodiments the separation step 3 includes adding a component to the second reaction product stream 300. In certain embodiments, this component causes a reduction in the solubility of the acid anhydride dissolved in the stream and results in precipitation of the acid anhydride. In some embodiments the added component is a crystallization nucleator for the acid anhydride. In certain embodiments, the crystallization nucleator comprises solid acid anhydride.

In some embodiments, the second reaction product stream 300 is near or above the saturation point of acid anhydride at particular reaction and reactor exit conditions. In some embodiments, separation of acid anhydride is accomplished by decreasing the temperature of the second reaction product stream 300. Because the second reaction product stream 300 is near or at the saturation point of acid anhydride in this embodiment, a relatively mild change in temperature or alternatively a decrease in pressure can cause a portion of the acid anhydride to crystallize or precipitate from the second reaction product stream 300.

In some embodiments, the separation method is crystallization, filtration or sedimentation. Separation may be accomplished with a variety of techniques including but not limited to evaporative cooling crystallization, cooling crystallization, flash drums, drying, filtering and combinations of these techniques. In some embodiments, the techniques and requisite equipment include: mixed suspension, mixed product removal, forced circulation evaporator crystallizer, draft tube crystallizer, draft tube crystallizer, surface cooled crystallizer, direct contact refrigeration crystallizer, classified suspension crystallizers, mixed suspension-classified product removal crystallizer, Oslo type crystallizer, scraped surface crystallizer, batch or semi-batch crystallization, recompression-evaporative crystallizer Selection will be based in part on crystal size sought, as well as the process flow conditions.

In certain embodiments where filtration is the solid-liquid separation technique, the filtration is performed under carbon monoxide pressure. Without being bound by theory or limiting the scope of the claimed invention, it is believed that the carbonylation catalysts described herein may decompose in the absence of CO. Therefore, filtering under conditions that maintain a substantial pressure of CO can be advantageous to the lifetime of the catalyst and the total productivity of the process. In certain embodiments the filtration is performed at a CO pressure ranging from about 15 psi to about 5000 psi. In certain embodiments, the filtration is performed under a CO pressure in the range from about 15 psi to about 1200 psi, from about 60 psi to about 800 psi, from about 100 psi to about 600 psi, from about 200 psi to about 600 psi, or from about 50 psi to about 500 psi.

In some embodiments where filtration is the solid-liquid separation technique, continuous filtration methods and equipment can be used including, but not limited to rotary drum filters, filter presses, disc filters and vacuum filters. Selection of equipment and operating conditions will depend in part based on flow rates, viscosities, temperatures and pressure, as well as the desired properties of the end products.

Gas-Liquid Separation

In some embodiments, the separation step 3 includes separating acid anhydride in the vapor phase (e.g., distillation, flashing, etc.). In some embodiments, the solvent present in the second reaction product stream 300 has a lower vapor pressure than the acid anhydride. In this instance, the acid anhydride product will be separated by heating the second reaction product stream 300, boiling the acid anhydride out of the second reaction product stream 300. Additionally, or alternatively, the acid anhydride product will be separation by reducing the pressure of the second reaction product stream 300.

Liquid-Liquid Separation

In some embodiments, separation of the acid anhydride is accomplished through liquid-liquid extraction. The extraction process involves partitioning the second reaction product stream 300 into two immiscible solvents. In the extraction, a portion of the acid anhydride will be partitioned into one solvent and the other solvent will contain at least the reaction catalyst. In some embodiments, after the extraction, the solvent containing acid anhydride product will be the acid anhydride product stream 400, and the stream containing the catalyst will be the recycle stream 500.

In some embodiments, one of the solvents is or includes the reaction solvent. In some embodiments, only one solvent is added for the separation step 3 via extraction. In some embodiments, the recycle stream 500 contains the reaction solvent. In some embodiments, the recycle stream 500 contains the reaction solvent and the other added solvent, contains the acid anhydride.

In some embodiments, one or both of the extraction solvents are ionic liquids. In some embodiments, one of the solvents is an aqueous solvent. In some embodiments, the extraction is counter current extraction, in some embodiments the extraction is co-current extraction. In some embodiments the extraction is a multi-stage extraction. Again, as described above, the recycling stream 500 may be further treated after extraction but before it is combined with the feed stream 100 or added to the first carbonylation reactor 110.

In some embodiments, after the separation step 3 the acid anhydride product stream 400 is subject to further processing, refinement or treatment. In some embodiments, the further processing further isolates the acid anhydride. The acid anhydride product stream 400 may be increased or decreased in temperature or pressure. The acid anhydride product stream 400 may be filtered or other otherwise treated to prepare the acid anhydride product stream 400 for further reaction or product storage.

Conversion to Dicarboxylic Acid or Further Products

Acid anhydride product stream 400 may undergo further reaction to covert the acid anhydride to a dicarboxylic acid 4. Reaction chemistry for the conversion to a dicarboxylic acid is well known, and may include reaction of the acid anhydride with water at elevated temperatures to produce a dicarboxylic acid product 700.

Additionally, or alternatively, the acid anhydride product stream 400, may undergo further reaction to convert it to other useful compounds. In particular, four-carbon compounds are contemplated as the ultimate reaction product, including, but not limited to 1,4 butanediol (BDO), THF, or gamma-butyrolactone (GBL) in addition to succinic acid. Suitable reaction schemes for production of the 4-carbon compounds can be achieved by substituting succinic anhydride for the maleic anhydride used as a feedstock in known routes to these compounds. For example, the 1,4 butanediol is currently produced by the reaction of maleic anhydride with methanol, and hydrogenation of intermediate products of the anhydride-methanol reaction. Replacing maleic anhydride in this reaction scheme with succinic anhydride from the processes herein, reduces the number hydrogenation steps required to make BDO by one.

Therefore, in one aspect, the present invention encompasses continuous methods for the production of succinic anhydride from ethylene oxide incorporating the concepts described above. In certain embodiments, such methods include the steps of:

contacting ethylene oxide with carbon monoxide in the presence of a carbonylation catalyst in a first reaction zone to provide a first product containing beta propiolactone, residual ethylene oxide, and the carbonylation catalyst;

feeding the first product stream to a second reaction zone, where the stream is contacted with additional carbon monoxide under conditions sufficient to convert the residual ethylene oxide to beta propiolactone and to convert a substantial portion of the beta propiolactone to succinic anhydride, to provide a second product stream comprising dissolved succinic anhydride and carbonylation catalyst;

treating the second product stream such that the concentration of succinic anhydride in the stream exceeds the solubility of succinic anhydride;

separating solid succinic anhydride from the second product stream to produce a succinic anhydride product stream comprising solid succinic anhydride and a liquid catalyst recycling stream comprising the dissolved catalyst and dissolved succinic anhydride; and returning the catalyst recycling stream to an inlet of the first reaction zone.

In certain embodiments, this method is characterized in that the first reaction zone comprises at least one continuous stirred tank reactor. In certain embodiments, one or more of the continuous stirred tank reactor or reactors is or are operated at steady state conditions. In certain embodiments, the first reaction zone comprises a series of two or more continuous stirred tank reactors where each reactor is characterized in that it has a lower steady state ethylene oxide concentration than the reactor preceding it in the series.

In certain embodiments of this method is characterized in that the second reaction zone comprises one or more plug flow reactors. In certain embodiments, the plug flow reactors are operated under conditions to convert essentially all of the beta propiolactone in the reaction zone to succinic anhydride.

In a certain embodiments, the first reaction zone comprises at least one continuous stirred tank reactor and the second reaction zone comprises at least one plug flow reactor.

In certain embodiments, the second reaction zone is operated at higher CO pressure and/or higher temperature than the first reaction zone.

In certain embodiments, the method is characterized in that the second reaction zone is operated at an elevated temperature. In certain embodiments, the step of treating the second product stream comprises cooling the stream. In certain embodiments, the step of treating the second product stream comprises cooling the stream by between about 10° C. and about 120° C. In certain embodiments, the step of treating the second product stream comprises cooling the stream by between about 20° C. and about 100° C., between about 20° C. and about 80° C., between about 10° C. and about 60° C., or between about 20° C. and about 40° C. In certain embodiments, the step of treating the second product stream comprises cooling the stream by about 10° C., about 20° C., about 30° C., about 40° C., about 60° C., about 80° C., or about 100° C.

In certain embodiments, the step of treating the second product stream comprises contacting the stream with seed crystals of succinic anhydride.

In certain embodiments, the step of separating solid succinic anhydride from the second product stream comprises filtering the stream to remove solids. In certain embodiments, the filtration is performed under a CO atmosphere. In certain embodiments, the filtration is performed under an atmosphere of CO characterized in that the partial pressure of CO is higher than 1 atmosphere (i.e. the filtration is a pressure filtration performed under CO). In certain embodiments, the filtration is performed under a CO pressure in the range from about 15 psi to about 5000 psi. In certain embodiments, the filtration is performed under a CO pressure in the range from about 15 psi to about 1200 psi, from about 60 psi to about 800 psi, from about 100 psi to about 600 psi, from about 200 psi to about 600 psi, or from about 50 psi to about 500 psi.

In certain embodiments, the filtering step provides a filtrate comprising the liquid catalyst recycling stream. In certain embodiments, the filtrate is characterized in that it is saturated in succinic anhydride. In certain embodiments, the filtrate is heated before the step of returning it to the first reaction zone. In certain embodiments, one or more components are added to the filtrate before returning it to the first reaction zone. In certain embodiments, ethylene oxide is added to the filtrate before it is returned to the first reaction zone. In certain embodiments, additional solvent is added to the filtrate before it is returned to the first reaction zone.

In certain embodiments, the method is characterized in that it is performed in the presence of a solvent. In certain embodiments, the solvent comprises 1,4 dioxane.

In certain embodiments, the method is characterized in that the catalyst comprises metal carbonyl compound and a Lewis acid. In certain embodiments, the catalyst comprises an anionic metal carbonyl compound and a cationic Lewis acid. In certain embodiments, the anionic metal carbonyl compound comprises $Co(CO)_4^-$. In certain embodiments, the cationic Lewis acid comprises a cationic metal complex. In certain embodiments the cationic metal complex comprises the combination of a metal atom and a multidentate ligand. In certain embodiments, cationic metal complex comprises the combination of a metal in the 3+ oxidation state and a dianionic tetradentate ligand. In certain embodiments, the cationic Lewis acid comprises aluminum. In certain embodiments, the cationic Lewis acid comprises chromium. In certain embodiments, the cationic Lewis acid comprises a substituted porphyrin ligand. In certain embodiments, the cationic Lewis acid comprises a substituted salen ligand. In certain embodiments, the cationic Lewis acid comprises a substituted salph ligand.

In certain embodiments, the method is characterized in that the first reaction zone contains a liquid reaction mixture at steady state (e.g. the composition of the liquid does not change substantially over time). In certain embodiments, the liquid reaction mixture comprises a mixture of 1,4 dioxane, ethylene oxide, beta propiolactone, succinic anhydride and a metal carbonyl catalyst. In certain embodiments, the dioxane comprises from about 10 weight percent to about 95 weight percent of the reaction mixture. In certain embodiments, the beta propiolactone comprises from about 1 to about 90 weight percent of the mixture. In certain embodiments, the ethylene oxide comprises from about 0.01 to about 10 weight percent of the mixture. In certain embodiments, the succinic anhydride comprises from about 4 to about 50 weight percent of the mixture.

In certain embodiments, the method includes an additional substep of removing a fraction of the catalyst recycling stream. This acts as a purge loop to prevent catalyst decomposition products from accumulating in the reactor. Typically, the quantity of catalyst removed in the purge is matched by a feed of fresh catalyst. This fresh catalyst makeup feed can be added back to the catalyst recycling stream prior to feeding the stream to the first reaction zone, or alternatively can be added directly at another inlet to the process. In certain embodiments, the catalyst catalyst makeup stream comprises a solution of catalyst in dioxane.

In certain embodiments, a method for the continuous production of succinic anhydride comprises the steps of: (a) contacting ethylene oxide with carbon monoxide in the presence of a carbonylation catalyst in a first reaction zone to provide a first product stream comprising beta propiolactone, residual ethylene oxide, and the carbonylation catalyst, wherein the carbonylation catalyst comprises a metal carbonyl compound, such as an anionic metal carbonyl compound, and a Lewis acid, such as the combination of a metal atom and a multidentate ligand; (b) feeding the first product stream to a second reaction zone, where the stream is contacted with additional carbon monoxide under conditions sufficient to convert substantially all of the residual ethylene oxide to beta propiolactone and to convert at least a portion of the beta propiolactone to succinic anhydride, to provide a second product stream comprising dissolved succinic anhydride and carbonylation catalyst; (c) treating the second product stream such that the concentration of succinic anhydride in the stream exceeds the solubility of succinic anhydride; (d) separating solid succinic anhydride from the second product stream to produce a succinic anhydride product stream comprising solid succinic anhydride and a liquid catalyst recycling stream comprising the dissolved catalyst and dissolved succinic anhydride; and (e) returning the liquid catalyst recycling stream to an inlet of the first reaction zone; wherein steps (a) and (b) are performed in the presence of a solvent.

In certain embodiments, a method for the continuous production of succinic anhydride comprises the steps of: (a) contacting ethylene oxide with carbon monoxide in the presence of a carbonylation catalyst in a first reaction zone to provide a first product stream comprising beta propiolactone, residual ethylene oxide, and the carbonylation catalyst, wherein the carbonylation catalyst comprises $Co(CO)_4^-$ and a cationic Lewis acid comprising the combination of a metal atom in the 3+ oxidation state, such as aluminum or chromium, and a multidentate ligand such as an optionally substituted porphyrin, an optionally substituted salen (N,N'-ethylenebis(salicylimine)) ligand, or an optionally substituted salph (N,N'-bis(2-hydroxybenzylidene)-1,2-benzenediamine) ligand; (b) feeding the first product stream to a second reaction zone, where the stream is contacted with additional carbon monoxide under conditions sufficient to convert substantially all of the residual ethylene oxide to beta propiolactone and to convert at least a portion of the beta propiolactone to succinic anhydride, to provide a second product stream comprising dissolved succinic anhydride and carbonylation catalyst; (c) treating the second product stream such that the concentration of succinic anhydride in the stream exceeds the solubility of succinic anhydride; (d) separating solid succinic anhydride from the second product stream to produce a succinic anhydride product stream comprising solid succinic anhydride and a liquid catalyst recycling stream comprising the dissolved catalyst and dissolved succinic anhydride; and (e) returning the liquid catalyst recycling stream to an inlet of the first reaction zone; wherein steps (a) and (b) are performed in the presence of a solvent comprising 1,4 dioxane.

In certain embodiments, a method for the continuous production of succinic anhydride comprises the steps of: (a) contacting ethylene oxide with carbon monoxide in the presence of a carbonylation catalyst in a first reaction zone to provide a first product stream comprising beta propiolactone, residual ethylene oxide, and the carbonylation catalyst, wherein the carbonylation catalyst comprises $Co(CO)_4^-$ and a cationic Lewis acid comprising the combination of aluminum or chromium and a multidentate ligand such as an optionally substituted porphyrin, an optionally substituted salen (N,N'-ethylenebis(salicylimine)) ligand, or an optionally substituted salph (N,N'-bis(2-hydroxybenzylidene)-1,2-benzenediamine) ligand, e.g., the carbonylation catalyst comprises $[(TPP)Al(THF)_2][Co(CO)_4]$; (b) feeding the first product stream to a second reaction zone, where the stream is contacted with additional carbon monoxide under conditions sufficient to convert substantially all of the residual ethylene oxide to beta propiolactone and to convert at least a portion of the beta propiolactone to succinic anhydride, to provide a second product stream comprising dissolved succinic anhydride and carbonylation catalyst; (c) treating the second product stream such that the concentration of succinic anhydride in the stream exceeds the solubility of succinic anhydride; (d) separating solid succinic anhydride from the second product stream to produce a succinic anhydride product stream comprising solid succinic anhydride and a liquid catalyst recycling stream comprising the dissolved catalyst and dissolved succinic anhydride, wherein said separating comprises filtering the stream to remove solid succinic anhydride; and (e) returning the liquid catalyst recycling stream to an inlet of the first reaction zone; wherein steps (a) and (b) are performed in the presence of a solvent comprising 1,4 dioxane.

In certain embodiments, a method for the continuous production of succinic anhydride comprises the steps of: (a) contacting ethylene oxide with carbon monoxide in the presence of a carbonylation catalyst in a first reaction zone to provide a first product stream comprising beta propiolactone, residual ethylene oxide, and the carbonylation catalyst, wherein the carbonylation catalyst comprises $Co(CO)_4^-$ and a cationic Lewis acid comprising the combination of aluminum or chromium and a multidentate ligand such as an optionally substituted porphyrin, an optionally substituted salen (N,N-ethylenebis(salicylimine)) ligand, or an optionally substituted salph (N,N'-bis(2-hydroxybenzylidene)-1,2-benzenediamine) ligand, e.g., the carbonylation catalyst comprises $[(TPP)Al(THF)_2][Co(CO)_4]$; (b) feeding the first product stream to a second reaction zone, where the stream is contacted with additional carbon monoxide under conditions sufficient to convert substantially all of the residual ethylene oxide to beta propiolactone and to convert at least a portion of the beta propiolactone to succinic anhydride, to provide a second product stream comprising dissolved succinic anhydride and carbonylation catalyst; (c) treating the second product stream such that the concentration of succinic anhydride in the stream exceeds the solubility of succinic anhydride, wherein said treating comprises contacting the stream with seed crystals of succinic anhydride; (d) separating solid succinic anhydride from the second product stream to produce a succinic anhydride product stream comprising solid succinic anhydride and a liquid catalyst recycling stream comprising the dissolved catalyst and dissolved succinic anhydride, wherein said separating comprises filtering the stream to remove solid succinic anhydride, and wherein said filtering is optionally performed under a CO atmosphere, e.g., under a CO pressure in the range from about 15 psi to about 5000 psi; and (e) returning the liquid catalyst recycling stream to an inlet of the first reaction zone; wherein steps (a) and (b) are performed in the presence of a solvent comprising 1,4 dioxane.

In certain embodiments, a method for the continuous production of succinic anhydride comprises the steps of: (a) contacting ethylene oxide with carbon monoxide in the presence of a carbonylation catalyst in a first reaction zone to provide a first product stream comprising beta propiolactone, residual ethylene oxide, and the carbonylation catalyst, wherein the carbonylation catalyst comprises $Co(CO)_4^-$ and a cationic Lewis acid comprising the combination of aluminum or chromium and a multidentate ligand such as an optionally substituted porphyrin, an optionally substituted salen (N,N'-ethylenebis(salicylimine)) ligand, or an optionally substituted salph (N,N'-bis(2-hydroxybenzylidene)-1,2-benzenediamine) ligand, e.g., the carbonylation catalyst comprises $[(TPP)Al(THF)_2][Co(CO)_4]$; (b) feeding the first product stream to a second reaction zone, where the stream is contacted with additional carbon monoxide under conditions sufficient to convert substantially all of the residual ethylene oxide to beta propiolactone and to convert at least a portion of the beta propiolactone to succinic anhydride, to provide a second product stream comprising dissolved succinic anhydride and carbonylation catalyst, wherein the second reaction zone is operated at an elevated temperature; (c) cooling the second product stream such that the concentration of succinic anhydride in the stream exceeds the solubility of succinic anhydride; (d) separating solid succinic anhydride from the second product stream to produce a succinic anhydride product stream comprising solid succinic anhydride and a liquid catalyst recycling stream comprising the dissolved catalyst and dissolved succinic anhydride, wherein said separating comprises filtering the stream to remove solid succinic anhydride, and wherein said filtering is optionally performed under a CO atmosphere, e.g., under a CO pressure in the range from about 15 psi to about 5000 psi; and (e) returning the liquid catalyst recycling stream to an inlet of the first reaction zone; wherein steps (a) and (b) are performed in the presence of a solvent comprising 1,4 dioxane.

EXAMPLES

Materials handling common to all examples: 1,4-Dioxane was dried over Na/benzophenone ketyl and degassed in open vacuum. 1,4-dioxane, $[(TPP)Al(THF)_2][Co(CO)_4]$, and ethylene oxide (EO) were handled under dry nitrogen using a drybox or standard Schlenk line techniques.

Example 1

Recycling Reaction

Figure 5:
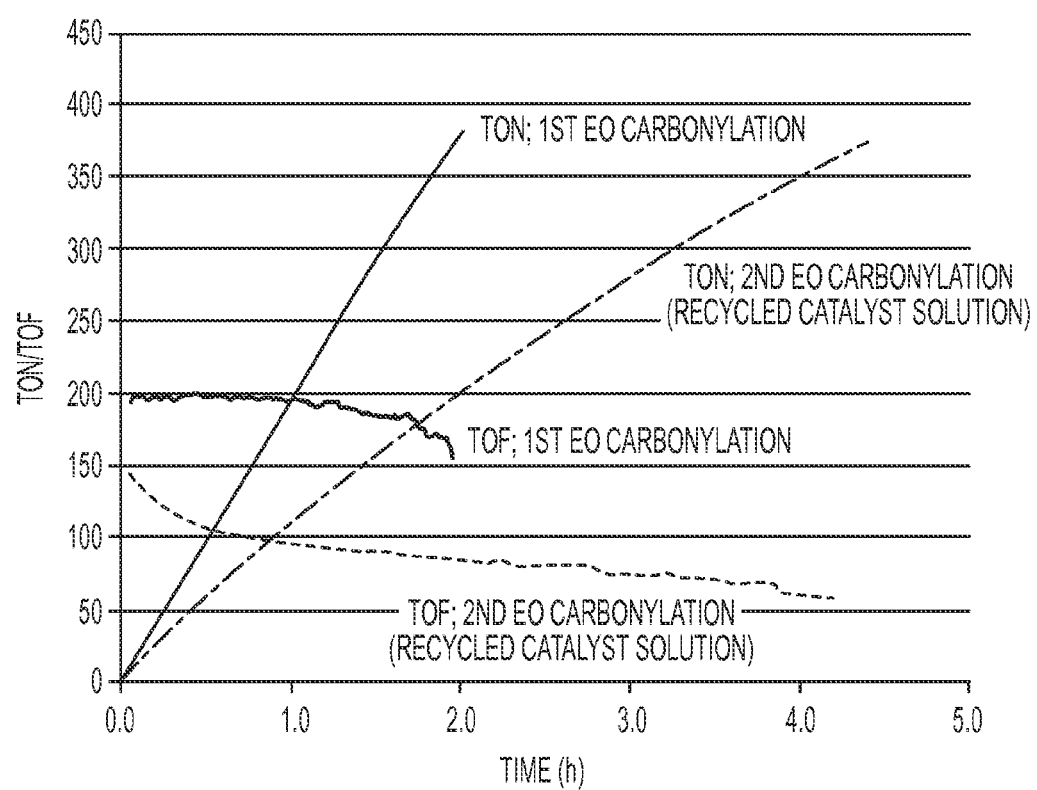
FIG. 5 shows catalyst effectiveness through two cycles of converting ethylene epoxide to succinic anhydride with the same recycled catalyst.

In a nitrogen drybox, a 300 ml high pressure reactor, fitted with an in-line attenuated total reflectance infrared spectroscopy ("ATR IR") probe was charged with $[(TPP)Al(THF)_2][Co(CO)_4]$ catalyst (0.36 mmol; TPP= tetraphenylporphyrinato), sealed, then removed from the drybox. The reactor was then further charged with 114 mL of 1,4-dioxane under $N_2$, mechanically stirred at 500 rpm, heated to 37° C., and pressured to 200 psi of carbon monoxide, CO. Ethylene oxide ("EO") (120 mmol) was charged into a shot tank that was connected to the reactor. The shot tank was pressurized with 600 psi of CO, and EO was added to the reactor by opening the valve connecting the shot tank and the reactor. The reactor was stirred at 37° C. under 600 psi of CO for 20 h. The reaction was monitored by in-line ATR-IR. After the reaction, the reactor was vented to release CO. The reactor was brought into a nitrogen drybox, and opened. The reaction mixture containing crystalline SA was filtered through a frit. Then, 95 mL of the filtrate was added back to the reactor. The SA concentration in the filtrate was 0.52 M as determined by quantitative gas chromatography (GC). The reactor was sealed, and then removed from the drybox. The reactor was stirred at 500 rpm, heated to 37° C., and pressured to 200 psi of CO. Another shot of EO (100 mmol) was charged into the shot tank. EO was added with 600 psi of CO to the reactor by opening the valve connecting the shot tank and the reactor. The reactor was stirred at 37° C. under 600 psi of CO for 24 h. The reaction was monitored by in-line ATR-IR. The result is summarized in Table 1 and FIG. 5.

TABLE 1

Concentrations of ethylene epoxide, succinic anhydride and turnover frequency for two additions of ethylene epoxide to carbonylation reaction.

| carbonylation | EO (mmol) | Total Volume (mL) | $[SA]_0^*$ (M) | $TOF_{init}^*$ (h−1) | Catalyst |
|---|---|---|---|---|---|
| 1st | 120 | 120 | 0 | 198 | fresh |
| 2nd | 100 | 100 | 0.52 | 136 | recycled |

*$[SA]_0$: succinic anhydride concentration at the start of each double carbonylation
$TOF_{init}$: turnover frequency of EO carbonylation (EO to BPL) during the first 5 minutes in each double carbonylation.

Example 2

Multiple EO Addition

Figure 6:
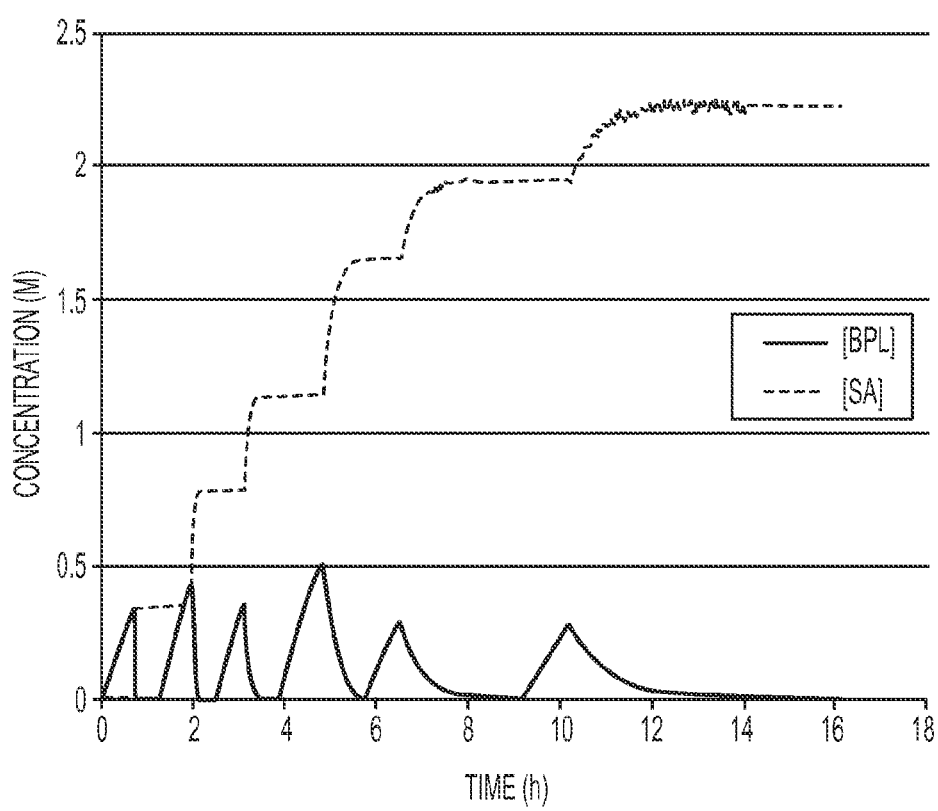
FIG. 6 shows succinic anhydride concentration in the reaction mixture and that the succinic acid concentration has little effect on the rate of EO carbonylation.

In a nitrogen drybox, a 300 ml reactor fitted with an in-line ATR IR probe was charged with [(TPP)Al(THF)$_2$][Co(CO)$_4$] catalyst (0.30 mmol; TPP=tetraphenylporphyrinato), sealed, then removed from the drybox. The reactor was then further charged with 97 mL of 1,4-dioxane under N$_2$, mechanically stirred at 500 rpm, heated to 37° C., and pressured to 200 psi of CO. Ethylene oxide (34.8 mmol) was charged into a shot tank that was connected to the reactor. The shot tank containing ethylene oxide was pressurized with 600 psi of CO. Ethylene oxide was added to the reactor by opening the valve connecting the shot tank and the reactor. The reactor was stirred at 37° C. under 600 psi of CO. The reaction was monitored by in-line ATR-IR. After the beta-propiolactone is all converted to SA, CO pressure inside the reactor was reduced to 550 psi by venting CO. The shot tank was recharged with ethylene oxide (42.4 mmol), and pressurized with 600 psi of CO. The second shot of EO was added to the reactor by opening the valve connecting the shot tank and the reactor. EO conversion to SA was monitored by in-line ATR. EO addition and double carbonylation were repeated 4 more times (Table 2). The in-line ATR-IR result (FIG. 6) shows that succinic anhydride concentration in the reaction mixture has little effect on the rate of EO carbonylation.

TABLE 2

Concentrations of ethylene epoxide, succinic anhydride and turnover frequency for repeated additions of ethylene epoxide to carbonylation reaction

| Addition | EO (mmol) | $[SA]_0^*$ (M) | $TOF_{init}^*$ (h$^{-1}$) |
|---|---|---|---|
| 1st | 34.8 | 0 | 168 |
| 2nd | 42.4 | 0.35 | 225 |
| 3rd | 37.1 | 0.77 | 234 |
| 4th | 54.4 | 1.13 | 218 |
| 5th | 31.3 | 1.65 | 152 |
| 6th | 30.8 | 1.94 | 112 |

*$[SA]_0$: succinic anhydride concentration at the start of each double carbonylation
$TOF_{init}$: turnover frequency of EO carbonylation (EO to BPL) during the first 5 minutes in each double carbonylation.

Example 3

5000-Fold Scale Up

In a first reactor 7.5 kg/hr of ethylene oxide is fed. The first reactor is operated at steady state conditions, with 1.5 M concentration of succinic anhydride present in the reactor volume. Additionally, 485 L/hr of solvent containing 1.5 mol/hr of [(TPP)Al(THF)$_2$][Co(CO)$_4$] catalyst (1.4 kg/hr) catalyst is fed to the reactor. The reactor is maintained at a pressure of 200 psig of carbon monoxide. The reactor is sized such that the feed and solvent have a residence time of at least 2.5 hours. (e.g., 1500 L in volume). Under these conditions, about 174 mole/hr of beta-propiolactone is produced. (12.5 kg/hr).

The beta-lactone is fed directly, with the solvent and catalyst, to a second reactor, also maintained at a pressure of 200 psig of carbon monoxide. The second reactor is sized such that reactants have a residence time of at least 15 minutes (e.g., 125 L in volume). The second reactor produces approximately, 174 mole/hr of succinic anhydride. (17.4 kg/hr). The concentration of succinic anhydride increases from approximately 1.5 M to 1.64 M From the second reactor, the product stream, containing succinic anhydride, solvent, catalyst, unreacted reactants and byproducts is passed to a crystallizer, which crystallizes the succinic anhydride at a rate of 174 mole per hr, resulting a final product stream of 17.4 kg/hr. The remaining succinic anhydride in the total amount of solvent with the catalyst and returned to the first reactor.

Other Embodiments

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

What is claimed is:

1. A method for the continuous production of an acid anhydride, the method comprising the steps of:
   a) contacting an epoxide with carbon monoxide, optionally in the presence of a carbonylation catalyst in a first reaction zone to provide a first product stream comprising a beta-lactone, residual epoxide, and, if present, the carbonylation catalyst;
   b) feeding the first product stream to a second reaction zone, where the stream is contacted with additional carbon monoxide under conditions sufficient to convert substantially all of the residual epoxide to the beta-lactone and to convert a portion of the beta-lactone to an acid anhydride, to provide a second product stream comprising dissolved acid anhydride and, if present, carbonylation catalyst;

c) treating the second product stream such that the concentration of the acid anhydride in the stream exceeds the solubility of the acid anhydride;

d) separating solid acid anhydride from the second product stream to produce an acid anhydride product stream comprising solid acid anhydride and a liquid catalyst recycling stream comprising the dissolved catalyst, if present, and dissolved acid anhydride; and e) returning the liquid catalyst recycling stream to an inlet of the first reaction zone, wherein the acid anhydride is a succinic anhydride.

2. The method according to claim 1 for the continuous production of succinic anhydride, the method comprising the steps of:

a) contacting ethylene oxide with carbon monoxide in the presence of a carbonylation catalyst in a first reaction zone to provide a first product stream comprising beta propiolactone, residual ethylene oxide, and the carbonylation catalyst;

b) feeding the first product stream to a second reaction zone, where the stream is contacted with additional carbon monoxide under conditions sufficient to convert substantially all of the residual ethylene oxide to beta propiolactone and to convert at least a portion of the beta propiolactone to succinic anhydride, to provide a second product stream comprising dissolved succinic anhydride and carbonylation catalyst;

c) treating the second product stream such that the concentration of succinic anhydride in the stream exceeds the solubility of succinic anhydride;

d) separating solid succinic anhydride from the second product stream to produce a succinic anhydride product stream comprising solid succinic anhydride and a liquid catalyst recycling stream comprising the dissolved catalyst and dissolved succinic anhydride; and e) returning the liquid catalyst recycling stream to an inlet of the first reaction zone.

3. The method of claim 1, wherein the first reaction zone comprises at least one continuous stirred tank reactor.

4. The method of claim 3, wherein at least one continuous stirred tank reactor in the first reaction zone is operated at steady state conditions.

5. The method of claim 3, wherein the first reaction zone comprises a series of two or more continuous stirred tank reactors where each reactor is characterized in that it has a lower steady state epoxide concentration than the reactor preceding it in the series.

6. The method of claim 1, wherein the second reaction zone comprises one or more plug flow reactors.

7. The method of claim 6, wherein the at least one plug flow reactor in the second reaction zone is operated under conditions to convert essentially all of the beta-lactone in the reaction zone to acid anhydride.

8. The method of claim 1, wherein the first reaction zone comprises at least one continuous stirred tank reactor and the second reaction zone comprises at least one plug flow reactor.

9. The method of claim 1, wherein the first reaction zone comprises a plurality of continuous stirred tank reactors and the second reaction zone comprises at least one plug flow reactor.

10. The method of claim 1, wherein the second reaction zone is operated at higher CO pressure and/or higher temperature than the first reaction zone.

11. The method of claim 1, wherein the second reaction zone is operated at an elevated temperature.

12. The method of claim 11, wherein the step of treating the second product stream comprises cooling the stream.

13. The method of claim 12, wherein the second product stream is cooled by between about 10° C. and about 120° C.

14. The method of claim 13, wherein the second product stream is cooled by between about 20° C. and about 100° C., between about 20° C. and about 80° C., between about 10° C. and about 60° C., or between about 20° C. and about 40° C.

15. The method of claim 12, wherein the second product stream is cooled by about 10° C., about 20° C., about 30° C., about 40° C., about 60° C., about 80° C., or about 100° C.

16. The method of claim 1, wherein the step of treating the second product stream comprises contacting the stream with seed crystals of the acid anhydride.

17. The method of claim 1, wherein the step of separating solid acid anhydride from the second product stream comprises filtering the stream to remove solid acid anhydride.

18. The method of claim 17, wherein the filtration is performed under a CO atmosphere.

19. The method of claim 18, wherein the filtration is performed under a CO pressure in the range from about 15 psi to about 5000 psi.

20. The method of claim 19, wherein the filtration is performed under a CO pressure in the range from about 15 psi to about 1200 psi, from about 60 psi to about 800 psi, from about 100 psi to about 600 psi, from about 200 psi to about 600 psi, or from about 50 psi to about 500 psi.

21. The method of claim 17, wherein the filtering step provides a filtrate comprising the liquid catalyst recycling stream characterized in that it is saturated in the acid anhydride.

22. The method of claim 21, wherein the filtrate is heated before the step of returning it to an inlet of the first reaction zone.

23. The method of claim 1, characterized in that steps a) and b) are performed in the presence of a solvent.

24. The method of claim 23, wherein the solvent comprises 1,4 dioxane.

25. The method of claim 1, wherein the carbonylation catalyst comprises metal carbonyl compound and a Lewis acid.

26. The method of claim 1, wherein the carbonylation catalyst comprises an anionic metal carbonyl compound and a cationic Lewis acid.

27. The method of claim 26, wherein the anionic metal carbonyl compound comprises $Co(CO)_4^-$.

28. The method of claim 26, wherein the cationic Lewis acid comprises the combination of a metal atom and a multidentate ligand.

29. The method of claim 28, wherein the cationic Lewis acid comprises the combination of a metal atom in the 3+ oxidation state and a dianionic tetradentate ligand.

30. The method of claim 26, wherein the cationic Lewis acid comprises aluminum.

31. The method of claim 26, wherein the cationic Lewis acid comprises chromium.

32. The method of claim 26, wherein the cationic Lewis acid comprises an optionally substituted porphyrin ligand.

33. The method of claim 26, wherein the cationic Lewis acid comprises an optionally substituted salen ligand.

34. The method of claim 26, wherein the cationic Lewis acid comprises an optionally substituted salph ligand.

35. The method of claim 2, wherein the first reaction zone contains a liquid reaction mixture at steady state, the liquid reaction mixture comprising a mixture of 1,4 dioxane, ethylene oxide, beta propiolactone, succinic anhydride and a metal carbonyl catalyst.

36. The method of claim 35, wherein the 1,4 dioxane comprises from about 10 weight percent to about 95 weight percent of the reaction mixture, the beta propiolactone comprises from about 1 to about 90 weight percent of the mixture, the ethylene oxide comprises from about 0.01 to about 10 weight percent of the mixture, and the succinic anhydride comprises from about 4 to about 50 weight percent of the mixture.

37. The method of claim 1, further comprising the step of removing a fraction of the catalyst recycling stream from the system.

38. The method of claim 37, wherein the quantity of catalyst removed is replaced by a feed of fresh catalyst.

39. The method of claim 1, wherein the succinic anhydride is selected from the group consisting of succinic anhydride, methylsuccinic anhydride, chloromethylsuccinic anhydride, and ethylsuccinic anhydride.

\* \* \* \* \*